United States Patent
Berthier et al.

(10) Patent No.: US 10,876,078 B2
(45) Date of Patent: Dec. 29, 2020

(54) PROCESS FOR THE PREPARATION OF MICROCAPSULES

(71) Applicant: Firmenich SA, Geneva (CH)

(72) Inventors: Damien Berthier, Geneva (CH); Geraldine Leon, Geneva (CH); Lahoussine Ouali, Geneva (CH)

(73) Assignee: Firmenich SA, Satigny (CH)

( * ) Notice: Subject to any disclaimer, the term of this patent is extended or adjusted under 35 U.S.C. 154(b) by 48 days.

(21) Appl. No.: 16/320,121

(22) PCT Filed: Jul. 26, 2017

(86) PCT No.: PCT/EP2017/068931
§ 371 (c)(1),
(2) Date: Jan. 24, 2019

(87) PCT Pub. No.: WO2018/019908
PCT Pub. Date: Feb. 1, 2018

(65) Prior Publication Data
US 2019/0233765 A1    Aug. 1, 2019

(30) Foreign Application Priority Data
Jul. 27, 2016 (EP) .................................. 16181389

(51) Int. Cl.
| | | |
|---|---|---|
| *C11D 3/37* | (2006.01) | |
| *A61Q 13/00* | (2006.01) | |
| *A61K 8/11* | (2006.01) | |
| *B01J 13/16* | (2006.01) | |
| *C11D 3/50* | (2006.01) | |
| *C11D 17/00* | (2006.01) | |
| *A61K 8/87* | (2006.01) | |
| *B01J 13/20* | (2006.01) | |

(52) U.S. Cl.
CPC .............. *C11D 3/3726* (2013.01); *A61K 8/11* (2013.01); *A61K 8/87* (2013.01); *A61Q 13/00* (2013.01); *B01J 13/16* (2013.01); *B01J 13/206* (2013.01); *C11D 3/3703* (2013.01); *C11D 3/505* (2013.01); *C11D 17/0039* (2013.01); *A61K 2800/412* (2013.01)

(58) Field of Classification Search
CPC ...... A61K 8/11; A61K 2800/412; A61K 8/87; C11D 3/505; C11D 17/0039
See application file for complete search history.

(56) References Cited

U.S. PATENT DOCUMENTS

| | | | |
|---|---|---|---|
| 3,577,515 A | 5/1971 | Vandegaer | |
| 6,211,258 B1 * | 4/2001 | Eling | C08G 18/22 521/170 |
| 2007/0042182 A1 * | 2/2007 | Markus | A01N 25/28 428/402.2 |
| 2014/0135253 A1 * | 5/2014 | Bellouard-Drevet | B01J 13/16 512/4 |
| 2014/0342625 A1 * | 11/2014 | Murray | C08K 3/20 442/81 |
| 2015/0252312 A1 | 9/2015 | De Villeneuve et al. | |
| 2017/0216166 A1 * | 8/2017 | Sasaki | C11D 3/505 |
| 2018/0078468 A1 * | 3/2018 | Jerri | A61K 8/8158 |
| 2018/0087132 A1 * | 3/2018 | Park | C22C 21/08 |

FOREIGN PATENT DOCUMENTS

| | | |
|---|---|---|
| CN | 1805784 A | 7/2006 |
| DE | 2342066 A1 | 3/1974 |
| EP | 633059 A1 | 1/1995 |
| WO | 1994029603 A1 | 12/1994 |
| WO | 1997044125 A1 | 11/1997 |
| WO | 1998021254 A1 | 5/1998 |
| WO | 2000064860 A1 | 11/2000 |
| WO | 2004098767 A1 | 11/2004 |
| WO | 2007096790 A1 | 8/2007 |
| WO | 2011154893 A1 | 12/2011 |
| WO | 2013000587 A1 | 1/2013 |
| WO | 2013068255 A1 | 5/2013 |
| WO | 2013085882 A1 | 6/2013 |

OTHER PUBLICATIONS

International Search Report and Written Opinion, application PCT/EP2017/068931, dated Sep. 8, 2017.

* cited by examiner

*Primary Examiner* — John R Hardee
(74) *Attorney, Agent, or Firm* — Armstrong Teasdale LLP

(57) ABSTRACT

The present invention relates to a new process for the preparation of melamine-formaldehyde free microcapsules. Microcapsules obtainable by said process are also an object of the invention. Perfuming compositions and consumer products comprising said capsules, in particular perfumed consumer products in the form of home care or personal care products, are also part of the invention.

11 Claims, No Drawings

PROCESS FOR THE PREPARATION OF MICROCAPSULES

CROSS-REFERENCE

This application is a 371 filing of International Patent Application PCT/EP2017/068931 filed 26 Jul. 2017, which claims the benefit of European patent application 16181389.4, filed 27 Jul. 2016, the contents of which are hereby incorporated by reference in their entirety.

TECHNICAL FIELD

The present invention relates to a new process for the preparation of melamine-formaldehyde free microcapsules. Microcapsules obtainable by said process are also an object of the invention. Perfuming compositions and consumer products comprising said capsules, in particular perfumed consumer products in the form of home care or personal care products, are also part of the invention.

BACKGROUND OF THE INVENTION

One of the problems faced by the perfumery industry lies in the relatively rapid loss of olfactive benefit provided by odoriferous compounds due to their volatility, particularly that of "top-notes". In order to tailor the release rates of volatiles, delivery systems such as microcapsules containing a perfume are needed to protect and later release the core payload when triggered. A key requirement from the industry regarding these systems is to survive suspension in challenging bases without physically dissociating or degrading. This is referred to as stability for the delivery system. For instance, fragranced personal and household cleansers containing high levels of aggressive surfactant detergents are very challenging for the stability of microcapsules.

Aminoplast microcapsules formed of a melamine-formaldehyde resin have been largely used to encapsulate hydrophobic actives, thus protecting said actives and providing their controlled release. However, capsules such as aminoplast ones suffer from stability problems when used in consumer products comprising surfactants, such as perfumery consumer products, especially after prolonged storage at elevated temperatures. In such products, even though the capsule wall remains intact, the encapsulated active tends to leak out of the capsule by diffusion through the wall due to the presence of surfactants that are able to solubilise the encapsulated active in the product base. The leakage phenomenon reduces the efficiency of the capsules to protect the active and provide its controlled release.

A variety of strategies have been described to improve the stability of oil core-based microcapsules. Cross-linking of capsule walls, with chemical groups such as polyamines and polyisocyanates, has been described as a way to improve stability of microcapsules. WO2011/154893 discloses for instance a process for the preparation of polyurea microcapsules using a combination of aromatic and aliphatic polyisocyanates in specific relative concentrations. Compared to aminoplast, polyurea-based microcapsules present the additional advantage of being free from melamine-formaldehyde. However, these capsules are not always satisfactory in terms of mechanical properties as they are less friable, which can negatively impact their olfactive performance represented by the odor intensity perceived during handling and after intentional breakage e.g. by rubbing.

WO2013/068255 is also proposing a solution to develop "formaldehyde-free" capsules, which responds to an increasing demand from the industry due to regulatory concerns. The described capsules are obtained by a process including the use of an oligomeric composition prepared by reacting a polyamine component with an aldehyde and a protic acid catalyst, then forming an emulsion with the oligomeric composition, an oil and a cross-linker, before finally heating and cooling. The polyamine component is essential in the disclosed process as it participates to the structure of the wall and to the performance of the capsules in terms of reduction of oil leakage. However, the use of a polyamine in such a process can limit the application scope of the obtained capsules as some components may not be tolerated.

There is still a need to simplify processes and recipes, and to use more eco-friendly materials, while not compromising on the performance of the capsules, in particular in terms of stability in a challenging medium such as a consumer product base, as well as in delivering a good performance in terms of active ingredient delivery, e.g. olfactive performance in the case of perfuming ingredients. The present invention is proposing a solution to the above-mentioned problem, based on a new process for the preparation of microcapsules, said process being performed in the absence of a polyamine component, using a combination of a bio-sourced polymer with specific acids.

SUMMARY OF THE INVENTION

It has now been surprisingly found, that performing melamine-formaldehyde free microcapsules encapsulating active ingredients could be obtained without using an amine or polyamine, by combining an anionic bio-sourced polyol with a specific protic acid catalyst. The process of the invention therefore provides a solution to the above-mentioned problems as it allows preparing poly(urea-urethane) capsules with a simplified recipe using bio-sourced materials. Unexpectedly, the applicant has found that only specific acids allowed obtaining capsules with the desired stability in challenging bases. In particular, acetic acid which has been widely disclosed as a protic acid component in polycondensation processes does not lead to stable microcapsules with the process of the invention.

In a first aspect, the present invention relates to a process for the preparation of melamine-formaldehyde free poly(urea-urethane) core-shell microcapsules slurry comprising the steps of:
1) admixing an oil, preferably comprising a perfume or flavour, with at least one polyisocyanate having at least three isocyanate functional groups to form an oil phase, provided that the oil phase is essentially free from diisocyanate;
2) preparing a water phase under acidic conditions, preferably at pH below 4.5, comprising at least one anionic bio-sourced polyol and a catalyst comprising a protic acid having a pKa below 4.5;
3) adding the oil phase to the water phase to form an oil-in-water dispersion;
4) performing a curing step to form a microcapsule slurry;
5) optionally adding at least one cationic copolymer to the capsule slurry; said process being performed without substantial amount of amine or polyamine being added at any stage of the process.

In a second aspect, the invention relates to a melamine-formaldehyde free poly(urea-urethane) microcapsule comprising an oil-based core, a shell consisting essentially of a polymerised polyisocyanate formed from at least one polyisocyanate comprising at least three isocyanate functional groups and an anionic bio-sourced polyol, obtainable by a process as defined above.

A perfuming composition comprising
(i) microcapsules as defined above, wherein the oil comprises a perfume;
(ii) at least one ingredient selected from the group consisting of a perfumery carrier and a perfumery co-ingredient; and
(iii) optionally at least one perfumery adjuvant is another object of this invention.

A consumer product comprising:
a) from 2 to 65% by weight, relative to the total weight of the consumer product, of at least one surfactant;
b) water or a water-miscible hydrophilic organic solvent; and
c) microcapsules or a perfuming composition as defined above, is also part of the invention.

DETAILED DESCRIPTION OF THE INVENTION

Unless stated otherwise, percentages (%) are meant to designate a percentage by weight of a composition.

By, "no substantial amount of amine or poly amine being added at any stage of the process" it is meant that if present, the amount of amine or polyamine added has to be sufficiently low so as not to be able to significantly change the properties of the microcapsule shell if it reacts with the polyisocyanate. Typically, the amount of amine functionalities that can be added in the process of the present invention is less than 50% molar, preferably less than 25% molar, most preferably less than 10% molar of the amount of isocyanate functionalities.

According to a particular embodiment, no amine or polyamine is added at any stage of the process.

By "active ingredient", it is meant a single compound or a combination of ingredients.

By "perfume or flavour oil", it is meant a single perfuming or flavouring compound or a mixture of several perfuming or flavouring compounds.

By "bio-sourced polyol" it is meant a chemically modified polyol from polyol produced by living organisms. Bio-sourced polyol include natural and artificial components and are characterized by molecular weight distributions ranging from 1,000 (1 thousand) to 1,000,000,000 (1 billion) Daltons. These macromolecules may be carbohydrates (sugar based) or proteins (amino-acid based) or a combination of both (gums) and can be linear, cross-linked or branched.

By "consumer product" or "end-product" it is meant a manufactured product ready to be distributed, sold and used by a consumer.

Glyoxylic acid and 2-oxoacetic acid are used indifferently in the present invention.

For the sake of clarity, by the expression "dispersion" in the present invention it is meant a system in which particles are dispersed in a continuous phase of a different composition and it specifically includes a suspension or an emulsion.

It has been found that melamine-formaldehyde free microcapsules with overall good performance namely a right balance between stability in a surfactant-based product and delivery of the active ingredient e.g. odor perception in the case of a perfume, could be obtained without adding a (poly)amine by using a combination of anionic bio-sourced polymer with particular catalyst acid. This is surprising in view of the fact that it was never disclosed that the nature of the acid could impact the stability of capsules obtained by similar processes, combined with the fact that the only processes describing polyurea-based capsules without the addition of a polyamine so far were either using a diisocyanate as an essential ingredient due to its reactivity, or were teaching away from using triisocyanate as the obtained capsules were then described as having a low performance in particular high oil leakage upon storage.

The present invention therefore relates in a first aspect to a process for the preparation of a melamine-formaldehyde free poly(urea-urethane) core-shell microcapsule slurry comprising the steps of:
1) admixing an oil comprising an active ingredient, preferably a perfume or flavour, with at least one polyisocyanate having at least three isocyanate functional groups to form an oil phase, provided that the oil phase is essentially free from diisocyanate;
2) preparing a water phase under acidic conditions, preferably at pH below 4.5, comprising at least one anionic biosourced polyol and a catalyst comprising a protic acid having a pKa below 4.5;
3) adding the oil phase to the water phase to form an oil-in-water dispersion;
4) performing a curing step to form a microcapsule slurry;
5) optionally adding at least one cationic copolymer to the capsule slurry; said process being performed without substantial amount of amine or polyamine being added at any stage of the process.

It has been thus found that in the absence of a diisocyanate, and in the absence of amine, a polyisocyanate comprising at least three isocyanate functional groups in presence of specific acid conditions and with a particular emulsifier, being a biosourced polyol, was capable of polymerisation with sufficient efficiency to provide a capsule wall with good properties.

In one step of the process, an oil phase is formed by admixing at least one hydrophobic active ingredient with at least one polyisocyanate, provided that the oil phase is essentially free from diisocyanate.

Hydrophobic active ingredients are preferably chosen from the group consisting of flavor, flavor ingredients, perfume, perfume ingredients, nutraceuticals, cosmetics, insect control agents, biocide actives and mixtures thereof.

According to a particular embodiment, the hydrophobic-active ingredient comprises a mixture of a perfume with another ingredient selected from the group consisting of nutraceuticals, cosmetics, insect control agents and biocide actives.

According to a particular embodiment, the hydrophobic active ingredient comprises a perfume.

According to a particular embodiment, the hydrophobic active ingredient consists of a perfume.

By "perfume" (or also "perfume oil") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odour. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodour counteraction, antimicrobial effect, microbial stability, insect control.

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or *sulphurous* heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

According to any one of the invention's embodiments, the hydrophobic active ingredients represent between about 10% and 60% w/w, or even between 20% and 45% w/w, by weight, relative to the total weight of the dispersion as obtained after step 3).

Suitable polyisocyanates used according to the invention include aromatic polyisocyanate, aliphatic polyisocyanate and mixtures thereof. Said polyisocyanate comprises at least 3 but may comprise up to 6, or even only 4, isocyanate functional groups.

According to a particular embodiment, a triisocyanate (3 isocyanate functional group) is used.

According to one embodiment, said polyisocyanate is an aromatic polyisocyanate. The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets, polyisocyanurates and trimethylol propane adducts of diisocyanates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

According to another embodiment, said polyisocyanate is an aliphatic polyisocyanate. The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

According to another embodiment, said at least one polyisocyanate is in the form of a mixture of at least one aliphatic polyisocyanate and of at least one aromatic polyisocyanate, both comprising at least three isocyanate functional groups, such as a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate. Preferably, when used as a mixture the molar ratio between the aliphatic polyisocyanate and the aromatic polyisocyanate is ranging from 80:20 to 10:90.

According to an embodiment, the at least one polyisocyanate used in the process of the invention is present in amounts representing from 1 to 15%, preferably from 2 to 8% and more preferably from 2 to 6% of the oil phase.

According to an embodiment, the oil phase is free from diisocyanate.

According to a particular embodiment, the oil phase essentially consists of the polyisocyanate with at least 3 isocyanate functional groups, and a perfume or flavor oil.

In another step of the process according to the invention, an anionic biosourced polyol and a protic acid having a pKa below 4.5 are mixed to form a water phase under acidic conditions. According to a preferred embodiment, the pH of the water phase is below 4.5.

According to a particular embodiment, the anionic biosourced polyol is selected from the group consisting of lignin, lignin sulfate, carboxymethyl cellulose, alginic acid sodium salt, polygalacuronic acid, dextran sulphate sodium salt and mixtures thereof.

According to an embodiment, the protic acid is selected from the group consisting of glyoxylic acid, citric acid, tartaric acid, fumaric acid, salicylic acid, sulfuric acid, phosphoric acid, nitric acid, formic acid, chlorohydric acid, malic acid, lactic acid, oxalic acid and mixtures thereof.

According to a preferred embodiment, the protic acid having a pKa below 4.5 is selected from the group consisting of glyoxylic acid, citric acid, tartaric acid, fumaric acid, salicylic acid, oxalic acid, malic acid, lactic acid, formic acid and mixtures thereof. According to a particular embodiment, the protic acid having a pKa below 4.5 consists of glyoxylic acid.

According to an embodiment, the catalyst comprises at least 50% of a protic acid having a pKa below 4.5.

According to a particular embodiment, the catalyst consists of a protic acid having a pKa below 4.5.

According to a particular embodiment, the catalyst is free from metal salts, in particular free from tin salts.

According to any one of the above embodiments of the present invention, the dispersion comprises between about 0.5% and 2.5% w/w of anionic bio-sourced polyol, percentage being expressed on a w/w basis relative to the total weight of the dispersion as obtained after step 3).

According to one embodiment of the invention, the water phase is cured at 45-60° C. for 1 to 4 hours.

In another step of the process of the invention, the oil phase is then added to the water phase to form a dispersion, wherein the mean droplet size is preferably comprised between 1 and 1000 µm, more preferably between 1 and 500 µm, and even more preferably between 5 and 50 microns. This is followed by a curing step 4) which allows ending up with microcapsules in the form of a slurry or liquid dispersion. According to a preferred embodiment, said step is performed at a temperature comprised between 60 and 80° C., possibly under pressure, for 1 to 4 hours. More preferably it is performed at between 50 and 90° C. for between 30 minutes and 4 hours.

According to a particular embodiment of the invention, at the end of step 4) one may also add to the invention's slurry a polymer selected from cationic polymer and mixtures thereof to form an outer coating to the microcapsules.

Cationic polymers are well known to a person skilled in the art. Preferred cationic polymers have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination. The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 3.5M Dalton, more preferably between 50,000 and 1.5M Dalton. According to a particular embodiment, one will use cationic polymers based on acrylamide, methacrylamide, N-vinylpyrrolidone, quaternized N,N-dimethylaminomethacrylate, diallyldimethylammonium chloride, quaternized vinylimidazole (3-methyl-1-vinyl-1H-imidazol-3-ium chloride), vinylpyrrolidone, acrylamidopropyltrimonium chloride, *cassia* hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. Preferably copolymers shall be selected from the group consisting of polyquaternium-5, polyquaternium-6, polyquaternium-7, polyquaternium10, polyquaternium-11, polyquaternium-16, polyquaternium-22, polyquaternium-28, polyquaternium-43, polyquaternium-44, polyquaternium-46, *cassia* hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. As specific examples of commercially available products, one may cite Salcare® SC60 (cationic copolymer of acrylamidopropyltrimonium chloride and acrylamide, origin: BASF) or Luviquat®, such as the PQ 11N, FC 550 or Style (polyquaternium-11 to 68 or quaternized copolymers of vinylpyrrolidone origin: BASF), or also the Jaguar® (C13S or C17, origin Rhodia).

According to any one of the above embodiments of the invention, there is added an amount of polymer described above comprised between about 0% and 5% w/w, or even between about 0.1% and 2% w/w, percentage being expressed on a w/w basis relative to the total weight of the slurry as obtained after step 4). It is clearly understood by a person skilled in the art that only part of said added polymers will be incorporated into/deposited on the microcapsule shell.

Alternatively, in the optional step 5), the slurry obtained by the process described above can be submitted to a drying, like spray-drying, to provide the microcapsules as such, i.e. in a powdery form. It is understood that any standard method known by a person skilled in the art to perform such drying is also applicable. In particular the slurry may be spray-dried preferably in the presence of a polymeric carrier material such as polyvinyl acetate, polyvinyl alcohol, dextrins, natural or modified starch, vegetable gums, pectins, xanthans, alginates, carragenans or cellulose derivatives to provide microcapsules in a powder form.

Melamine-formaldehyde free poly(urea-urethane) microcapsules comprising a core comprising an oil, a shell consisting essentially of a polymerised polyisocyanate formed from at least one polyisocyanate comprising at least three isocyanate functional groups, and an anionic biosourced polyol, obtainable by the process above-described are also an object of the invention. Despite the nature of the polyisocyanate forming the membrane and despite the absence of any polyamine, the capsules of the invention show very good performance in terms of stability in challenging medium and active-ingredient delivery.

In this regard it has to be mentioned that although ideal situation would be one where microcapsules show best stability, i.e. lowest active leakage in application combined with best delivery performance, such as perfume intensity in the case of a perfume in application both before rubbing and after rubbing, different scenarios can be very interesting depending on the application and slightly less stable capsules with higher odor performance can be very useful and so could more stable capsules with slightly lower odor performance. The capsules of the invention have a profile perfume leakage/odor performance that varies depending on the proportion of polyisocyanate and the nature of the perfume oil. A skilled person in the art is capable of choosing the best balance depending on the needs in application. The capsules according to the invention present the additional advantage of being free from melamine-formaldehyde.

Another object of the present invention is a perfuming composition comprising:

(i) microcapsules as defined above, wherein the oil comprises a perfume;

(ii) at least one ingredient selected from the group consisting of a perfumery carrier, a perfumery co-ingredient and mixtures thereof;

(iii) optionally at least one perfumery adjuvant.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to at least impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.1 and 30% by weight of microcapsules as defined above.

The invention's microcapsules can advantageously be used in many application fields and used in consumer products. Microcapsules can be used in liquid form applicable to liquid consumer products as well as in powder form, applicable to powder consumer products.

Another object of the present invention is a liquid consumer product comprising:
a) from 2 to 65% by weight, relative to the total weight of the consumer product, of at least one surfactant;
b) water or a water-miscible hydrophilic organic solvent; and
c) microcapsules as defined above,
  d) optionally non-encapsulated perfume.
A powder consumer product comprising
(a) from 2 to 65% by weight, relative to the total weight of the consumer product, of at least one surfactant;
(b) microcapsules as defined above.
(c) optionally perfume powder that is different from the microcapsules defined above is also an object according to the present invention.

In the case of microcapsules including a perfume oil-based core, the products of the invention, can in particular be of used in perfumed consumer products such as product belonging to fine fragrance or "functional" perfumery. Functional perfumery includes in particular personal-care products including hair-care, body cleansing, skin care, hygiene-care as well as home-care products including laundry care and air care. Consequently, another object of the present invention consists of a perfumed consumer product comprising as a perfuming ingredient, the microcapsules defined above or a perfuming composition as defined above. The perfume element of said consumer product can be a combination of perfume microcapsules as defined above and free or non-encapsulated perfume, as well as other types of perfume microcapsule than those here-disclosed.

In particular a liquid consumer product comprising:
a) from 2 to 65% by weight, relative to the total weight of the consumer product, of at least one surfactant;
b) water or a water-miscible hydrophilic organic solvent; and
c) a perfuming composition as defined above is another object of the invention.

Also a powder consumer product comprising
(a) from 2 to 65% by weight, relative to the total weight of the consumer product, of at least one surfactant; and
(b) a perfuming composition as defined above is part of the invention.

The invention's microcapsules can therefore be added as such or as part of an invention's perfuming composition in a perfumed consumer product.

For the sake of clarity, it has to be mentioned that, by "perfumed consumer product" it is meant a consumer product which is expected to deliver among different benefits a perfuming effect to the surface to which it is applied (e.g. skin, hair, textile, paper, or home surface) or in the air (air-freshener, deodorizer etc). In other words, a perfumed consumer product according to the invention is a manufactured product which comprises a functional formulation also referred to as "base", together with benefit agents, among which an effective amount of microcapsules according to the invention.

The nature and type of the other constituents of the perfumed consumer product do not warrant a more detailed description here, which in any case would not be exhaustive, the skilled person being able to select them on the basis of his general knowledge and according to the nature and the desired effect of said product. Base formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Non-limiting examples of suitable perfumed consumer product can be a perfume, such as a fine perfume, a cologne, an after-shave lotion, a body-splash; a fabric care product, such as a liquid or solid detergent, tablets and pods, a fabric softener, a dryer sheet, a fabric refresher, an ironing water, or a bleach; a personal-care product, such as a hair-care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener or a "ready to use" powdered air freshener; or a home care product, such all-purpose cleaners, liquid or power or tablet dishwashing products, toilet cleaners or products for cleaning various surfaces, for example sprays & wipes intended for the treatment/refreshment of textiles or hard surfaces (floors, tiles, stone-floors etc.); a hygiene product such as sanitary napkins, diapers, toilet paper.

Preferably, the consumer product comprises from 0.1 to 15 wt %, more preferably between 0.2 and 5 wt % of the microcapsules of the present invention, these percentages being defined by weight relative to the total weight of the consumer product. Of course the above concentrations may be adapted according to the benefit effect desired in each product.

The capsules of the invention have proven to be particularly and advantageously stable in consumer products containing significant amount of surfactant and more particularly they demonstrated an improved stability compared to capsules wherein only one type of particles is used.

The invention will now be further described by way of examples. It will be appreciated that the invention as claimed is not intended to be limited in any way by these examples.

EXAMPLES

Example 1

Preparation of Microcapsules According to the Invention with Glyoxylic Acid and Carboxymethyl Cellulose Microcapsules A-1:

A solution of Ambergum™ 1221 (carboxymethyl cellulose, trademark from Hercules Inc.) in water was added in a beaker of 100 mL. The pH value was adjusted with glyoxylic acid to 3.73. This solution was kept at 25° C. before the preparation of the emulsion. A solution of perfume oil (Table 1) and polyisocyanate (see Table 2) was added into the beaker and shear with UltraTurrax at 24000 rpm for 2 min. The emulsion was transferred into a 250 mL reactor and heated at 45° C. for 1 h, then at 60° C. for 1 h, and finally at 80° C. for 3 h. The reaction mixture was cooled down to RT (pH=3.87). Relative proportions of raw materials are reported in Table 2.

TABLE 1

| perfume oil composition | |
|---|---|
| Raw material | wt % |
| Romascone ®[a] | 20 |
| Verdox ™[b] | 20 |
| Lorysia ®[c] | 20 |
| 3-(4-isopropylphenyl)-2-methylpropanal | 20 |
| Salicynile ®[d] | 20 |

[a]Methyl 2,2-dimethyl-6-methylene-1-cyclohexanecarboxylate, origin: Firmenich SA, Geneva, Switzerland
[b]2-tert-butyl-1-cyclohexyl acetate, trademark from International Flavors & Fragrances, USA
[c]4-(1,1-diméthyléthyl)-1-cyclohexyl acetate, origin: Firmenich SA, Geneva, Switzerland
[d](2Z)-2-phenyl-2-hexenenitrile, origin: Firmenich SA, Geneva, Switzerland

TABLE 2

| Capsule formulation | | |
|---|---|---|
| Raw materials | Amount (g) | % (w/w) |
| Water | To balance | To balance |
| Carboxymethyl cellulose (Ambergum ™ 1221, 4%) | 40.00 | 2.37 |
| 2-Oxoacetic acid (50%) | 0.57 | 0.42 |
| Perfume oil (Table 1) | 25.00 | 37.10 |
| Polyisocyanate [1] | 1.90 | 2.11 |
| Total | 67.47 | 100.00 |

[1] Takenate ® D-110N (75%) - trimethylol propane adduct of xylylene diisocyanate, trademark from: Mitsui Chemicals Microcapsules B-1

Microcapsules B-1 were prepared according to the protocol described for Microcapsules A-1. The solution of carboxymethyl cellulose and glyoxylic acid was heated at 45° C. for 1 h and cooled down to 25° C. before the preparation of the emulsion (final pH=3.69).

Microcapsules C-1

Microcapsules C-1 were prepared according to the protocol described for Microcapsules A-1. The solution of carboxymethyl cellulose and glyoxylic acid was heated at 45° C. for 2 h and cooled down to 25° C. before the preparation of the emulsion (final pH=3.85).

Microcapsules D-1

Microcapsules D-1 were prepared according to the protocol described for Microcapsules A-1. The solution of carboxymethyl cellulose and glyoxylic acid was heated at 60° C. for 1 h and cooled down to 25° C. before the preparation of the emulsion (final pH=3.82).

Microcapsules E-1

Microcapsules E-1 were prepared according to the protocol described for Microcapsules A-1. The solution of carboxymethyl cellulose and glyoxylic acid was heated at 60° C. for 2 h and cooled down to 25° C. before the preparation of the emulsion (final pH=3.81).

Microcapsules F-1

Microcapsules F-1 were prepared according to the conditions described for Microcapsules B-1. Regarding raw materials, a solution of perfume oil was prepared with 2.28 g of polyisocyanate (20% more NCO groups).

Microcapsules G-1

Microcapsules G-1 were prepared according to the conditions described for Microcapsules B-1. Regarding raw materials, a solution of perfume oil was prepared with 1.52 g of polyisocyanate (20% less NCO groups).

Microcapsules H-1

Microcapsules H-1 were prepared according to the conditions described for Microcapsules B-1. In terms of raw materials, the oil phase contained perfume oil, and as polyisocyanate, a mixture of Takenate® D110N (trimethylol propane adduct of xylylene diisocyanate, trademark from: Mitsui Chemicals) (0.95 g) and Desmodur® N100 (Biuret of hexamethylene diisocyanate (trademark from Bayer)) (0.95 g, final pH=3.90).

Microcapsules I-1

Microcapsules I-1 were prepared according to the protocol of Microcapsules B-1 with 50 g of solution of Ambergum™ 1221 (Hercules Inc) (25% more CMC) and 0.79 g of glyoxylic acid solution (pH=3.80).

Microcapsules J-1

Microcapsules J-1 were prepared according to the protocol of Microcapsules B-1 with 60 g of solution of Ambergum™ 1221 (Hercules Inc) (50% more CMC) and 0.89 g of glyoxylic acid solution (pH=3.80).

Example 2

Preparation of Capsules According to the Invention with Acids Having pKa<4.5

Microcapsules A-2

A solution of Ambergum™ 1221 (Hercules Inc) in water was added in a beaker of 100 mL. The pH value was adjusted with an aqueous solution of nitric acid to 4.05. This solution was kept at 45° C. for 1 h and then cooled down to 25° C. A solution of perfume oil and polyisocyanate (see Table 3) was added into the beaker and both phases were sheared with UltraTurrax at 24000 rpm for 2 min. The emulsion was transferred into a 250 mL reactor and heat at 45° C. for 1 h, then at 60° C. for 1 h, and finally at 80° C. for 3 h. The reaction mixture was cooled down to RT (pH=4.01).

TABLE 3

Capsule formulation

| Raw materials | Amount (g) | % (w/w) |
|---|---|---|
| Water | To balance | To balance |
| Carboxymethyl cellulose [1] | 40.00 | 2.38 |
| Nitric acid (60%) | 0.25 | 0.22 |
| Perfume oil (Table 1) | 25.00 | 37.23 |
| Polyisocyanate [2] Takenate ® D-110N (75%) | 1.90 | 2.12 |
| Total | 67.15 | 100.00 |

[1] Ambergum™ 1221, 4%, Origin: Hercules Inc.
[2] Takenate® D-110N (75%) (trimethylol propane adduct of xylylene diisocyanate, trademark from: Mitsui Chemicals Microcapsules B-2

Microcapsules B-2 were prepared according to the protocol described for Microcapsules A-2 but the presence of sulfuric acid instead of nitric acid (96%, 0.15 g, final pH=3.94).

Microcapsules C-2

Microcapsules C-2 were prepared according to the protocol described for Microcapsules A-2 but in the presence of formic acid (99%, 0.16 g, final pH=3.92) instead of nitric acid.

Microcapsules D-2

Microcapsules D-2 were prepared according to the protocol described for Microcapsules A-2 but in the presence of an aqueous solution of hydrochloric acid (37%, 0.29 g, final pH=3.76) instead of nitric acid.

Microcapsules E-2

Microcapsules E-2 were prepared according to the protocol described for Microcapsules A-2 in the presence of an aqueous solution of phosphoric acid (84%, 0.29 g, final pH=4.04) instead of nitric acid.

Microcapsules F-2

Microcapsules F-2 were prepared according to the protocol described for Microcapsules A-2 in the presence of an aqueous solution of oxalic acid (0.1M, 15.40 g, final pH=4.03) instead of nitric acid.

Microcapsules G-2

Microcapsules G-2 were prepared according to the protocol described for Microcapsules A-2 in the presence of citric acid monohydrate (99.5%, origin: Acros organics, 0.35 g, final pH=4.14) instead of nitric acid.

Example 3

Preparation of Capsules According to the Invention

Microcapsules A-3:

A solution of alginic acid sodium salt (Alfa Aesar) in water was added in a beaker of 100 mL. The pH value was adjusted with glyoxylic acid to 3.79. This solution was kept at 25° C. before the preparation of the emulsion. A solution of perfume oil (Table 1) and polyisocyanate was added into the beaker and shear with UltraTurrax at 24000 rpm for 2 min. The emulsion was transferred into a 250 mL reactor and heated at 45° C. for 1 h, then at 60° C. for 1 h, and finally at 80° C. for 3 h. The reaction mixture was cooled down to RT (pH=3.79). Relative proportions of raw materials are reported in Table 4.

TABLE 4

Capsule formulation

| Raw materials | Amount (g) | % (w/w) |
|---|---|---|
| Water | To balance | To balance |
| Alginic acid sodium salt [1] | 40.00 | 2.37 |
| 2-Oxoacetic acid (50%) | 0.45 | 0.33 |
| Perfume oil (Table 1) | 25.00 | 37.12 |
| Polyisocyanate [2] | 1.90 | 2.12 |
| Total | 67.35 | 100.00 |

[1] Solution at 4% in water, Origin: Alfa Aesar A18565, very low viscosity.
[2] Takenate® D-110N (75%) - trimethylol propane adduct of xylylene diisocyanate, trademark from: Mitsui Chemicals Microcapsules B-3

Microcapsules B-3 were prepared according to the protocol described for Microcapsules A-3 in the presence of glyoxylic acid and a solution of alginic acid sodium salt affording aqueous solution with low viscosity (Origin: Alfa Aesar B25266, final pH=3.84).

Microcapsules C-3

Microcapsules C-3 were prepared according to the protocol described for Microcapsules A-3 in the presence of glyoxylic acid and a solution of polygalacturonic acid (Pectin, origin: Sigma, P3889, CAS RN 25990-10-7, final pH=2.21).

Microcapsules D-3

Microcapsules D-3 were prepared according to the protocol described for Microcapsules A-3 in the presence of glyoxylic acid and a solution of polygalacturonic acid (Pectin, origin: Sigma, P3850, CAS RN 9049-37-0, final pH=3.67).

Microcapsules E-3

Microcapsules E-3 were prepared according to the protocol described for Microcapsules A-3 in the presence of glyoxylic acid and a solution of dextran sulfate sodium salt (Origin: Sigma, D6924, CAS RN 9011-18-1, final pH=2.46).

Microcapsules F-3

Microcapsules F-3 were prepared according to the protocol described for Microcapsules A-3 in the presence of glyoxylic acid and a solution of dextran sulfate sodium salt (Origin: Sigma, 51227, final pH=3.77).

Example 4

Preparation of Capsules A-4 to E-4 Including a Cationic Copolymer

General Procedure

A solution of Ambergum™ 1221 (Hercules Inc.) in water (4 wt %, 40 g) was added in a beaker of 100 mL (Table 5). The pH value was adjusted with an aqueous solution of glyoxylic acid (50 wt %, 0.55 g) to 3.80. This solution was kept at 45° C. for 1 h and then cooled down to 25° C. A solution of perfume oil (Table 1) (25.00 g), Uvinul® A+(oil soluble UVA filter, Bayer) (1.25 g), and polyisocyanate-Takenate® D-110N ((75%) (trimethylol propane adduct of xylylene diisocyanate, trademark from: Mitsui Chemicals), 1.90 g-was added into the beaker and both phases were sheared with UltraTurrax at 24000 rpm for 2 min (pH=3.80). The emulsion was transferred into a 250 mL reactor and heat at 45° C. for 1 h, then at 60° C. for 1 h, and finally at 80° C. for 2 h. Aqueous solution of cationic copolymer of acrylamidopropyltrimonium chloride and acrylamide (Salcare® SC60, origin: BASF) (3 wt %, Table 5) was added and the dispersion was stirred at 80° C. for 1 h. The reaction mixture was finally cooled down to RT (pH=3.80).

TABLE 5

| Microcapsules | A-4 | B-4 | C-4 | D-4 | E-4 |
|---|---|---|---|---|---|
| Cationic copolymer [1] (g) | 5.0 | 10.50 | 17.00 | 25.00 | 35.00 |
| Cationic copolymer [1] (wt %) | 0.2 | 0.4 | 0.6 | 0.8 | 1.00 |

[1] cationic copolymer of acrylamidopropyltrimonium chloride and acrylamide (Salcare ® SC60, origin: BASF)

Example 5

Preparation of Capsules F-4 to R-4 with a Mixture of Cationic Copolymers

General Procedure

Capsules were prepared according to the protocol described for Capsules A-4. A mixture of aqueous solutions of cationic copolymer of acrylamidopropyltrimonium chloride and acrylamide (Salcare® SC60, origin: BASF) (3 wt %, 20 g) and a second copolymer (1wt %, Table 6) were added together and the dispersion was stirred at 80° C. for 1 h. The reaction mixture was finally cooled down to RT (pH=3.80).

TABLE 6

| Microcapsules | Copolymer | Solution (g) | Concentration (wt %) |
|---|---|---|---|
| F-4 | Jaguar C13S | 11.00 | 0.1 |
| G-4 | Jaguar C17AD | 11.00 | 0.1 |
| H-4 | Tinocare PQ760A | 22.00 | 0.2 |
| J-4 | Luviquat FC550 | 11.00 | 0.1 |
| K-4 | Luviquat FC370 | 11.00 | 0.1 |
| L-4 | Luviquat Style | 11.00 | 0.1 |
| M-4 | Luviquat Excellence | 22.00 | 0.2 |
| N-4 | N-Hance SP100 | 11.00 | 0.1 |
| O-4 | Polyquaternium 550 | 11.00 | 0.1 |
| P-4 | Polyquaternium 550 | 60.00 | 0.4 |
| Q-4 | Mirustyle CP | 11.00 | 0.1 |
| R-4 | Mirustyle MFP | 11.00 | 0.1 |

Example 6

Preparation of Microcapsules with Glyoxylic Acid, Acetic Acid and Carboxymethyl Cellulose Microcapsules B-6

A solution of carboxymethyl cellulose (Ambergum™ 1221; Hercules Inc.) in water was added in a beaker of 100 mL. A solution of acetic acid and glyoxylic acid at 50 wt % and 50 wt % respectively was prepared. The pH value of the aqueous phase was adjusted with this solution to 3.80 (1.06 g). The solution of carboxymethyl cellulose and acids was heated at 45° C. for 1 h and cooled down to 25° C. before the preparation of the emulsion. A solution of perfume oil and polyisocyanate (Table 7) was added into the beaker and shear with UltraTurrax at 24000 rpm for 2 min. The emulsion was transferred into a 250 mL reactor and heat at 45° C. for 1 h, then at 60° C. for 1 h, and finally at 80° C. for 3 h. The reaction mixture was cooled down to RT (pH=3.86).

TABLE 7

| Raw materials | Amount (g) | % (w/w) |
|---|---|---|
| Carboxymethyl cellulose[1] | 40.00 | 2.36 |
| Acetic acid and glyoxylic acid (50%) 50/50 w/w | 0.85 | 0.94 |
| Perfume oil (Table 1) | 25.00 | 36.90 |
| Polyisocyanate[2] | 1.90 | 2.10 |
| Water | To balance | 57.70 |
| Total | 67.75 | 100.00 |

[1] Ambergum™ 1221, 4%; Hercules Inc.
[2] Takenate® D-110N (75%) trademark from: Mitsui Chemicals; trimethylol propane adduct of xylylene diisocyanate Microcapsules C-6

Microcapsules C-6 were prepared according to the protocol of Microcapsules B-6 with acetic acid and glyoxylic acid at 25 wt % and 75 wt % respectively (pH=3.67).

TABLE 8

| Raw materials | Amount (g) | % (w/w) |
|---|---|---|
| Carboxymethyl cellulose[1] | 40.00 | 2.36 |
| Acetic acid and glyoxylic acid (50%) 25/75 w/w | 0.64 | 0.59 |
| Perfume oil (Table 1) | 25.00 | 37.02 |
| Polyisocyanate[2] | 1.90 | 2.11 |
| Water | To balance | 57.91 |
| Total | 67.54 | 100.00 |

[1] Ambergum™ 1221, 4%; Hercules Inc.
[2] Takenate® D-110N (75%) trademark from: Mitsui Chemicals; trimethylol propane adduct of xylylene diisocyanate Microcapsules E-6

Microcapsules E-6 were prepared according to the protocol of Microcapsules B-6 with acetic acid and glyoxylic acid at 10 wt % and 90 wt % respectively (pH=3.67).

TABLE 9

| Raw materials | Amount (g) | % (w/w) |
|---|---|---|
| Carboxymethyl cellulose[1] | 40.00 | 2.37 |
| Acetic acid and glyoxylic acid (50%) 10/90 w/w | 0.68 | 0.45 |
| Perfume oil (Table 1) | 25.00 | 37.00 |
| Polyisocyanate[2] | 1.90 | 2.11 |
| Water | To balance | 58.07 |
| Total | 67.58 | 100.00 |

[1] Ambergum™ 1221, 4%; Hercules Inc.
[2] Takenate® D-110N (75%) trademark from: Mitsui Chemicals; trimethylol propane adduct of xylylene diisocyanate Microcapsules F-6

Microcapsules F-6 were prepared according to the protocol of Microcapsules E-6 with 50 g of carboxymethyl cellulose solution.

TABLE 10

| Raw materials | Amount (g) | % (w/w) |
|---|---|---|
| Carboxymethyl cellulose[1] | 50.00 | 2.57 |
| Acetic acid and glyoxylic acid (50%) 10/90 w/w | 0.85 | 0.49 |
| Perfume oil (Table 1) | 25.00 | 32.15 |
| Polyisocyanate[2] | 1.90 | 1.83 |
| Water | To balance | 62.96 |
| Total | 77.75 | 100.00 |

[1] Ambergum™ 1221, 4%; Hercules Inc.
[2] Takenate® D-110N (75%) trademark from: Mitsui Chemicals; trimethylol propane adduct of xylylene diisocyanate Microcapsules G-6

Microcapsules G-6 were prepared according to the protocol of Microcapsules E-6 with 60 g of Carboxymethylcellulose solution.

TABLE 11

| Raw materials | Amount (g) | % (w/w) |
|---|---|---|
| Carboxymethyl cellulose [1] | 60.00 | 2.76 |
| Acetic acid and glyoxylic acid (50%) 10/90 w/w | 0.99 | 0.51 |
| Perfume oil (Table 1) | 25.00 | 28.77 |
| Polyisocyanate [2] | 1.90 | 1.64 |
| Water | To balance | 66.32 |
| Total | 86.89 | 100.00 |

[1] Ambergum™ 1221, 4%; Hercules Inc.
[2] Takenate® D-110N (75%) trademark from: Mitsui Chemicals; trimethylol propane adduct of xylylene diisocyanate Example 7

Preparation of Microcapsules with Acetic Acid and Carboxymethyl Cellulose

Comparative Microcapsules A-7

A solution of carboxymethyl cellulose (Ambergum™ 1221; Hercules Inc.) in water was added in a beaker of 100 mL. The pH value was adjusted with acetic acid to 4.01. This solution was kept at room temperature before the preparation of the emulsion. A solution of perfume oil and polyisocyanate was added into the beaker and shear with Ultra-Turrax at 24000 rpm for 2 min. The emulsion was transferred into a 250 mL reactor and heat at 45° C. for 1 h, then at 60° C. for 1 h, and finally at 80° C. for 3 h. The reaction mixture was cooled down to RT (pH=4.03).

TABLE 12

| Raw materials | Amount (g) | % (w/w) |
|---|---|---|
| Carboxymethyl cellulose [1] | 40.00 | 2.37 |
| Acetic acid | 0.70 | 1.04 |
| Perfume oil (Table 1) | 25.00 | 36.98 |
| Polyisocyanate [2] | 1.90 | 2.11 |
| Water | To balance | 57.50 |
| Total | 67.6 | 100.00 |

[1] Ambergum™ 1221, 4%; Hercules Inc.
[2] Takenate® D-110N (75%) trademark from: Mitsui Chemicals; trimethylol propane adduct of xylylene diisocyanate Comparative Microcapsules B-7

Comparative Microcapsules B-7 were prepared according to the protocol of Comparative Microcapsules A-7. The solution of carboxymethyl cellulose and acetic acid was heated at 45° C. for 1 h and cooled down to RT before the preparation of the emulsion (final pH=3.95).

Comparative Microcapsules C-7

Comparative Microcapsules C-7 were prepared according to the protocol of Comparative Microcapsules B-7. The solution of carboxymethyl cellulose and acetic acid was heated at 45° C. for 2 h before the preparation of the emulsion (final pH=3.99).

Comparative Microcapsules D-7

Comparative Microcapsules D-7 were prepared according to the protocol of Comparative Microcapsules B-7. The solution of carboxymethyl cellulose and acetic acid was heated at 60° C. for 1 h before the preparation of the emulsion (final pH=3.99).

Comparative Microcapsules E-7

Comparative Microcapsules E-7 were prepared according to the protocol of Comparative Microcapsules B-7. The solution of carboxymethyl cellulose and acetic acid was heated at 60° C. for 2 h before the preparation of the emulsion (final pH=3.91).

Comparative Microcapsules F-7

Comparative Microcapsules F-7 were prepared according to the protocol of Comparative Microcapsules A-7. A solution of perfume oil was prepared with 2.28 g of polyisocyanate (20% more NCO groups).

Comparative Microcapsules G-7

Comparative Microcapsules G-7 were prepared according to the protocol of Comparative Microcapsules F-7 with 1.52 g of polyisocyanate (20% less NCO groups).

Comparative Microcapsules H-7

A solution of carboxymethyl cellulose (Ambergum™ 1221; Hercules Inc.) in water was added in a beaker of 100 mL. The pH value was adjusted with acetic acid to 4.01. The solution of carboxymethyl cellulose and acetic acid was heated at 45° C. for 1 h and cooled down to 25° C. before the preparation of the emulsion. A solution of perfume oil, polyisocyanates (Table 13) was added into the beaker and shear with UltraTurrax at 24000 rpm for 2 min. The emulsion was transferred into a 250 mL reactor and heat at 45° C. for 1 h, then at 60° C. for 1 h, and finally at 80° C. for 3 h. The reaction mixture was cooled down to RT (pH=3.97).

TABLE 13

| Capsule formulation | | |
|---|---|---|
| Raw materials | Amount (g) | % (w/w) |
| Carboxymethyl cellulose [1] | 40.00 | 2.37 |
| Acetic acid | 0.70 | 1.04 |
| Perfume oil (Table 1) | 25.00 | 36.98 |
| Polyisocyanate 1 [2] | 1.90 | 1.90 |
| Polyisocyanate 2 [3] | 0.19 | 0.28 |
| Water | To balance | 57.43 |
| Total | 67.6 | 100.00 |

[1] Ambergum™ 1221, 4%; Hercules Inc.
[2] Takenate® D-110N (75%) trademark from: Mitsui Chemicals; trimethylol propane adduct of xylylene diisocyanate
[3] Biuret of hexamethylene diisocyanate (origin Bayer)

Comparative Microcapsules 1-7

Comparative Microcapsules 1-7 were prepared according to the protocol of Comparative Microcapsules H-7 with a solution of perfume oil with 0.95 g of polyisocyanates (Table 14) (pH=3.77).

TABLE 14

| Capsule formulation | | |
|---|---|---|
| Raw materials | Amount (g) | % (w/w) |
| Carboxymethyl cellulose[1] | 40.00 | 2.37 |
| Acetic acid | 0.70 | 1.04 |
| Perfume oil (Table 1) | 25.00 | 36.98 |
| Polyisocyanate 1 [2] | 0.95 | 1.05 |
| Polyisocyanate 2 [3] | 0.95 | 1.41 |
| Water | To balance | 57.15 |
| Total | 67.6 | 100.00 |

[1] Ambergum™ 1221, 4%; Hercules Inc.
[2] Takenate® D-110N (75%) trademark from: Mitsui Chemicals; trimethylol propane adduct of xylylene diisocyanate
[3] Biuret of hexamethylene diisocyanate (origin Bayer)

Example 8

Preparation of Microcapsules for Body-Care Application

General Protocol

A solution of carboxymethyl cellulose (Ambergum™ 1221, Hercules Inc) in water was added in a beaker of 100 mL. The pH value was adjusted with glyoxylic acid to 3.82. This solution was kept at 25° C. before the preparation of the emulsion. A solution of perfume oil (Table 15) and polyisocyanate was added into the beaker and shear with Ultra-Turrax at 24,000 rpm for 2 min. The emulsion was transferred into a 250 mL reactor and heat at 45° C. for 1 h, then at 60° C. for 1 h, and finally at 80° C. for 2 h. A solution of cationic polymer was added and the dispersion was stirred at 80° C. for one additional hour. The reaction mixture was cooled down to RT (pH=3.94).

TABLE 15 perfume oil composition in capsules of example 7

| Raw Materials | % in oil |
| --- | --- |
| Ethyl 2-methyl-pentanoate [1] | 4.00% |
| 2,4-Dimethyl-3-cyclohexene-1-carbaldehyde [1] | 4.00% |
| Allyl Heptanoate | 6.60% |
| (Z)-3-hexen-1-ol Butyrate | 1.30% |
| Allyl amyl glycolate | 13.10% |
| Delta Damascone | 2.00% |
| Verdyl acetate | 24.30% |
| Methylnaphtylcetone | 1.30% |
| Hedione ®[2] | 6.60% |
| Iso E Super ® [3] | 19.70% |
| Ald. Hexylcinnamique | 13.10% |
| Habanolide ® [4] | 4.00% |
| Total | 100% |

[1] Origin: Firmenich SA, Geneva, Switzerland
[2] Methyl dihydrojasmonate; origin and Trademark from Firmenich SA, Geneva, Switzerland
[3] 1-(octahydro-2,3,8,8-tetramethyl-2-naphtalenyl)-1-ethanone; origin International Flavors & Fragrances, USA Microcapsules A-8

Capsules of the present invention prepared with a cationic copolymer at 0.80%.

TABLE 16

Capsule formulation

| Raw materials | Amount (g) | % (w/w) |
| --- | --- | --- |
| Carboxymethyl cellulose [1] | 40.00 | 1.74 |
| Glyoxylic acid (50%) | 0.51 | 0.28 |
| Perfume oil (Table 15) | 25.00 | 27.20 |
| Polyisocyanate [2] | 1.90 | 1.55 |
| Cationic copolymer [3] | 24.50 | 0.80 |
| Water | To balance | 68.43 |
| Total | 91.91 | 100.00 |

[1] Ambergum ™ 1221, 4%; Hercules Inc.
[2] Takenate ® D-110N (75%) trademark from: Mitsui Chemicals; trimethylol propane adduct of xylylene diisocyanate
[3] Salcare ® SC60: origin and trademark from Ciba (acrylamidopropyltrimonium chloride/acrylamide copolymer), 3% solution in water Microcapsules B-8 Capsules of the present invention prepared with a mixture of cationic copolymers (Table 17).

TABLE 17

Capsule formulation

| Raw materials | Amount (g) | % (w/w) |
| --- | --- | --- |
| Carboxymethyl cellulose [1] | 40.00 | 1.62 |
| Glyoxylic acid (50%) | 0.57 | 0.29 |
| Perfume oil (Table 15) | 25.00 | 25.39 |
| Polyisocyanate [2] | 1.90 | 1.45 |
| Cationic copolymer 1 [3] | 20.00 | 0.61 |
| Cationic copolymer 1 [4] | 11.00 | 0.11 |
| Water | To balance | 70.53 |
| Total | 98.47 | 100.00 |

[1] Ambergum ™ 1221, 4%; Hercules Inc.
[2] Takenate ® D-110N (75%) trademark from: Mitsui Chemicals; trimethylol propane adduct of xylylene diisocyanate
[3] Salcare ® SC60: origin and trademark from Ciba (acrylamidopropyltrimonium chloride/acrylamide copolymer), 3% solution in water
[4] Guar Hydroxypropyltrimonium Chloride; solution 1%; Bayer Microcapsules C-8

Capsules of the present invention prepared with a cationic polymer at 0.40%.

TABLE 18

Capsule formulation

| Raw materials | Amount (g) | % (w/w) |
| --- | --- | --- |
| Carboxymethyl cellulose [1] | 40.00 | 2.05 |
| Glyoxylic acid (50%) | 0.57 | 0.37 |
| Perfume oil (Table 15) | 25.00 | 32.06 |
| Polyisocyanate [2] | 1.90 | 1.83 |
| Cationic polymer [3] | 10.50 | 0.40 |
| Water | To balance | 63.29 |
| Total | 98.47 | 100.00 |

[1] Ambergum ™ 1221, 4%; Hercules Inc.
[2] Takenate ® D-110N (75%) trademark from: Mitsui Chemicals; trimethylol propane adduct of xylylene diisocyanate
[3] Salcare ® SC60: origin and trademark from Ciba (acrylamidopropyltrimonium chloride/acrylamide copolymer), 3% solution in water Microcapsules D-8

Capsules of the present invention prepared with a mixture of two cationic copolymers.

TABLE 19

Capsule formulation

| Raw materials | Amount (g) | % (w/w) |
| --- | --- | --- |
| Carboxymethyl cellulose [1] | 40.00 | 1.62 |
| Glyoxylic acid (50%) | 0.57 | 0.29 |
| Perfume oil (Table 15) | 25.00 | 25.39 |
| Polyisocyanate [2] | 1.90 | 1.45 |
| Cationic polymer 1 [3] | 20.00 | 0.61 |
| Cationic polymer 2 [4] | 11.00 | 0.11 |
| Water | To balance | 70.53 |
| Total | 98.47 | 100.00 |

[1] Ambergum ™ 1221, 4%; Hercules Inc.
[2] Takenate ® D-110N (75%) trademark from: Mitsui Chemicals; trimethylol propane adduct of xylylene diisocyanate
[3] Salcare ® SC60: origin and trademark from Ciba (acrylamidopropyltrimonium chloride/acrylamide copolymer), 3% solution in water
[4] Jaguar ® C17, trademark from Rhodia (Guar Hydroxypropyltrimonium Chloride)

Microcapsules E-8

Capsules of the present invention prepared with a mixture of cationic polymers.

TABLE 20

| Capsule formulation | | |
|---|---|---|
| Raw materials | Amount (g) | % (w/w) |
| Carboxymethyl cellulose [1] | 40.00 | 1.46 |
| Glyoxylic acid (50%) | 0.57 | 0.26 |
| Perfume oil (Table 15) | 25.00 | 22.84 |
| Polyisocyanate [2] | 1.90 | 1.30 |
| Cationic polymer 1 [3] | 20.00 | 0.55 |
| Cationic polymer 2 [4] | 22.00 | 0.20 |
| Water | To balance | 73.39 |
| Total | 109.47 | 100.00 |

[1] Ambergum ™ 1221, 4%; Hercules Inc.
[2] Takenate ® D-110N (75%) trademark from: Mitsui Chemicals; trimethylol propane adduct of xylylene diisocyanate
[3] Salcare ® SC60: origin and trademark from Ciba (acrylamidopropyltrimonium chloride/acrylamide copolymer), 3% solution in water
[4] Tinocare PQ 760 A: origin and trademark from BASF (acrylamide/diallyldimethylammonium chloride and acrylamidopropyltrimonium chloride/acrylamide copolymer), 1% solution in water Microcapsules F-8

Capsules of the present invention prepared with a mixture of cationic polymers.

TABLE 21

| Capsule formulation | | |
|---|---|---|
| Raw materials | Amount (g) | % (w/w) |
| Carboxymethyl cellulose [1] | 40.00 | 1.62 |
| Glyoxylic acid (50%) | 0.57 | 0.29 |
| Perfume oil (Table 15) | 25.00 | 25.39 |
| Polyisocyanate [2] | 1.90 | 1.45 |
| Cationic polymer 1 [3] | 20.00 | 0.61 |
| Cationic polymer 2 [4] | 11.00 | 0.11 |
| Water | To balance | 70.53 |
| Total | 98.47 | 100.00 |

[1] Ambergum ™ 1221, 4%; Hercules Inc.
[2] Takenate ® D-110N (75%) trademark from: Mitsui Chemicals; trimethylol propane adduct of xylylene diisocyanate
[3] Salcare ® SC60: origin and trademark from Ciba (acrylamidopropyltrimonium chloride/acrylamide copolymer), 3% solution in water
[4] Luviquat ® PQ11: origin and trademark from BASF (1-vinylpyrrolidin-2-one/2-(acryloyloxy)-N-ethyl-N,N-dimethylethan-1-aminium ethyl sulfate copolymer), 1% solution in water.

Microcapsules G-8

Capsules of the present invention prepared with a mixture of cationic polymers.

TABLE 22

| Capsule formulation | | |
|---|---|---|
| Raw materials | Amount (g) | % (w/w) |
| Carboxymethyl cellulose [1] | 40.00 | 1.62 |
| Glyoxylic acid (50%) | 0.57 | 0.29 |
| Perfume oil (Table 15) | 25.00 | 25.39 |
| Polyisocyanate [2] | 1.90 | 1.45 |
| Cationic polymer 1 [3] | 20.00 | 0.61 |
| Cationic polymer 2 [4] | 11.00 | 0.11 |
| Water | To balance | 70.53 |
| Total | 98.47 | 100.00 |

[1] Ambergum ™ 1221, 4%; Hercules Inc.
[2] Takenate ® D-110N (75%) trademark from: Mitsui Chemicals; trimethylol propane adduct of xylylene diisocyanate
[3] Salcare ® SC60: origin and trademark from Ciba (acrylamidopropyltrimonium chloride/acrylamide copolymer), 3% solution in water
[4] Luviquat ® FC550: origin and trademark from BASF (3-methyl-1-vinyl-1H-imidazol-3-ium chloride/1-vinylpyrrolidin-2-one copolymer), 1% solution in water Microcapsules H-8

Capsules of the present invention prepared with a mixture of cationic polymers.

TABLE 23

| Capsule formulation | | |
|---|---|---|
| Raw materials | Amount (g) | % (w/w) |
| Carboxymethyl cellulose [1] | 40.00 | 1.62 |
| Glyoxylic acid (50%) | 0.57 | 0.29 |
| Perfume oil (Table 15) | 25.00 | 25.39 |
| Polyisocyanate [2] | 1.90 | 1.45 |
| Cationic polymer 1 [3] | 20.00 | 0.61 |
| Cationic polymer 2 [4] | 11.00 | 0.11 |
| Water | To balance | 70.53 |
| Total | 98.47 | 100.00 |

[1] Ambergum ™ 1221, 4%; Hercules Inc.
[2] Takenate ® D-110N (75%) trademark from: Mitsui Chemicals; trimethylol propane adduct of xylylene diisocyanate
[3] Salcare ® SC60: origin and trademark from Ciba (acrylamidopropyltrimonium chloride/acrylamide copolymer), 3% solution in water
[4] Merquat ® 550: origin and trademark from Nalco (acrylamide/diallyldimethylammonium chloride copolymer), 1% solution in water Microcapsules I-8

Capsules of the present invention prepared with a mixture of cationic polymers

TABLE 24

| Capsule formulation | | |
|---|---|---|
| Raw materials | Amount (g) | % (w/w) |
| Carboxymethyl cellulose [1] | 40.00 | 1.22 |
| Glyoxylic acid (50%) | 0.57 | 0.22 |
| Perfume oil (Table 15) | 25.00 | 19.02 |
| Polyisocyanate [2] | 1.90 | 1.08 |
| Cationic polymer 1 [3] | 20.00 | 0.46 |
| Cationic polymer 2 [4] | 44.00 | 0.33 |
| Water | To balance | 77.67 |
| Total | 131.47 | 100.00 |

[1] Ambergum ™ 1221, 4%; Hercules Inc.
[2] Takenate ® D-110N (75%) trademark from: Mitsui Chemicals; trimethylol propane adduct of xylylene diisocyanate
[3] Salcare ® SC60: origin and trademark from Ciba (acrylamidopropyltrimonium chloride/acrylamide copolymer), 3% solution in water
[4] Merquat ® 550: origin and trademark from Nalco (acrylamide/diallyldimethylammonium chloride copolymer), 1% solution in water Microcapsules J-8

Capsules of the present invention prepared with a mixture of cationic polymers.

TABLE 25

| Capsule formulation | | |
| --- | --- | --- |
| Raw materials | Amount (g) | % (w/w) |
| Carboxymethyl cellulose [1] | 40.00 | 1.62 |
| Glyoxylic acid (50%) | 0.57 | 0.29 |
| Perfume oil (Table 15) | 25.00 | 25.39 |
| Polyisocyanate [2] | 1.90 | 1.45 |
| Cationic polymer 1 [3] | 20.00 | 0.61 |
| Cationic polymer 2 [4] | 11.00 | 0.11 |
| Water | To balance | 70.53 |
| Total | 98.47 | 100.00 |

[1] Ambergum™ 1221, 4%; Hercules Inc.
[2] Takenate® D-110N (75%) trademark from: Mitsui Chemicals; trimethylol propane adduct of xylylene diisocyanate
[3] Salcare® SC60: origin and trademark from Ciba (acrylamidopropyltrimonium chloride/acrylamide copolymer), 3% solution in water
[4] Luviquat® Style: origin and trademark from BASF (3-methyl-1-vinyl-1H-imidazol-3-ium chloride/1-vinylpyrrolidin-2-one copolymer), 1% solution in water Microcapsules K-8

Capsules of the present invention prepared with a mixture of cationic polymers.

TABLE 26

| Capsule formulation | | |
| --- | --- | --- |
| Raw materials | Amount (g) | % (w/w) |
| Carboxymethyl cellulose 1) | 40.00 | 1.46 |
| Glyoxylic acid (50%) | 0.57 | 0.26 |
| Perfume oil (Table 15) | 25.00 | 22.84 |
| Polyisocyanate [2] | 1.90 | 1.30 |
| Cationic polymer 1 [3] | 20.00 | 0.55 |
| Cationic polymer 2 [4] | 22.00 | 0.20 |
| Water | To balance | 73.39 |
| Total | 109.47 | 100.00 |

1) Ambergum™ 1221, 4%; Hercules Inc.
[2] Takenate® D-110N (75%) trademark from: Mitsui Chemicals; trimethylol propane adduct of xylylene diisocyanate
[3] Salcare® SC60: origin and trademark from Ciba (acrylamidopropyltrimonium chloride/acrylamide copolymer), 3% solution in water
[4] Luviquat® Excellence: origin and trademark from BASF (3-methyl-1-vinyl-1H-imidazol-3-ium chloride/1-vinylpyrrolidin-2-one copolymer), 1% solution in water Microcapsules L-8

Capsules of the present invention prepared with phosphoric acid and a cationic polymer

TABLE 27

| Capsule formulation | | |
| --- | --- | --- |
| Raw materials | Amount (g) | % (w/w) |
| Carboxymethyl cellulose [1] | 40.00 | 1.58 |
| Phosphoric acid (84%) | 0.29 | 0.24 |
| Perfume oil (Table 15) | 25.00 | 24.71 |
| Polyisocyanate [2] | 1.90 | 1.41 |
| Cationic polymer [3] | 34.00 | 1.01 |
| Water | To balance | 71.05 |
| Total | 101.19 | 100.00 |

[1] Ambergum™ 1221, 4%; Hercules Inc.
[2] Takenate® D-110N (75%) trademark from: Mitsui Chemicals; trimethylol propane adduct of xylylene diisocyanate
[3] Salcare® SC60: origin and trademark from Ciba (acrylamidopropyltrimonium chloride/acrylamide copolymer), 3% solution in water Microcapsules M-8

Capsules of the present invention prepared with oxalic acid and a cationic polymer.

TABLE 28

| Capsule formulation | | |
| --- | --- | --- |
| Raw materials | Amount (g) | % (w/w) |
| Carboxymethyl cellulose [1] | 40.00 | 1.58 |
| Oxalic acid (0.78%) | 15.40 | 0.10 |
| Perfume oil (Table 15) | 25.00 | 21.50 |
| Polyisocyanate [2] | 1.90 | 1.23 |
| Cationic polymer [3] | 34.00 | 0.88 |
| Water | To balance | 74.71 |
| Total | 116.30 | 100.00 |

[1] Ambergum™ 1221, 4%; Hercules Inc.
[2] Takenate® D-110N (75%) trademark from: Mitsui Chemicals; trimethylol propane adduct of xylylene diisocyanate
[3] Salcare® SC60: origin and trademark from Ciba (acrylamidopropyltrimonium chloride/acrylamide copolymer), 3% solution in water Microcapsules N-8

Capsules of the present invention prepared with citric acid and a cationic polymer.

TABLE 29

| Capsule formulation | | |
| --- | --- | --- |
| Raw materials | Amount (g) | % (w/w) |
| Carboxymethyl cellulose [1] | 40.00 | 1.58 |
| Citric acid monohydrate (99.5%) | 0.35 | 0.34 |
| Perfume oil (Table 15) | 25.00 | 24.69 |
| Polyisocyanate [2] | 1.90 | 1.41 |
| Cationic polymer [3] | 34.00 | 1.01 |
| Water | To balance | 70.97 |
| Total | 101.25 | 100.00 |

[1] Ambergum™ 1221, 4%; Hercules Inc.
[2] Takenate® D-110N (75%) trademark from: Mitsui Chemicals; trimethylol propane adduct of xylylene diisocyanate
[3] Salcare® SC60: origin and trademark from Ciba (acrylamidopropyltrimonium chloride/acrylamide copolymer), 3% solution in water Microcapsules O-8

Capsules of the present invention prepared with malic acid and a cationic polymer

TABLE 30

| Capsule formulation | | |
| --- | --- | --- |
| Raw materials | Amount (g) | % (w/w) |
| Carboxymethyl cellulose [1] | 40.00 | 1.58 |
| DL-malic acid | 0.34 | 0.34 |
| Perfume oil (Table 15) | 25.00 | 24.69 |
| Polyisocyanate [2] | 1.90 | 1.41 |
| Cationic polymer [3] | 34.00 | 1.01 |
| Water | To balance | 70.97 |
| Total | 101.24 | 100.00 |

[1] Ambergum™ 1221, 4%; Hercules Inc.
[2] Takenate® D-110N (75%) trademark from: Mitsui Chemicals; trimethylol propane adduct of xylylene diisocyanate
[3] Salcare® SC60: origin and trademark from Ciba (acrylamidopropyltrimonium chloride/acrylamide copolymer), 3% solution in water Microcapsules P-8

Capsules of the present invention prepared with lactic acid and a cationic polymer

TABLE 31

| Capsule formulation | | |
| --- | --- | --- |
| Raw materials | Amount (g) | % (w/w) |
| Carboxymethyl cellulose [1] | 40.00 | 1.58 |
| L-lactic acid (90%) | 0.38 | 0.34 |
| Perfume oil (Table 15) | 25.00 | 24.68 |
| Polyisocyanate [2] | 1.90 | 1.41 |
| Cationic polymer [3] | 34.00 | 1.01 |
| Water | To balance | 70.98 |
| Total | 101.28 | 100.00 |

[1] Ambergum ™ 1221, 4%; Hercules Inc.
[2] Takenate ® D-110N (75%) trademark from: Mitsui Chemicals; trimethylol propane adduct of xylylene diisocyanate
[3] Salcare ® SC60: origin and trademark from Ciba (acrylamidopropyltrimonium chloride/acrylamide copolymer), 3% solution in water Microcapsules Q-8

Capsules of the present invention prepared with glyoxylic acid and a cationic polymer

TABLE 32

| Capsule formulation | | |
| --- | --- | --- |
| Raw materials | Amount (g) | % (w/w) |
| Carboxymethyl cellulose [1] | 40.00 | 1.58 |
| Glyoxylic acid (50%) | 0.51 | 0.25 |
| Perfume oil (Table 15) | 25.00 | 24.65 |
| Polyisocyanate [2] | 1.90 | 1.41 |
| Cationic polymer [3] | 34.00 | 1.01 |
| Water | To balance | 71.10 |
| Total | 101.41 | 100.00 |

[1] Ambergum ™ 1221, 4%; Hercules Inc.
[2] Takenate ® D-110N (75%) trademark from: Mitsui Chemicals; trimethylol propane adduct of xylylene diisocyanate
[3] Salcare ® SC60: origin and trademark from Ciba (acrylamidopropyltrimonium chloride/acrylamide copolymer), 3% solution in water Microcapsules R-8

Capsules of the present invention prepared with formic acid and a cationic polymer.

TABLE 33

| Capsule formulation | | |
| --- | --- | --- |
| Raw materials | Amount (g) | % (w/w) |
| Carboxymethyl cellulose [1] | 40.00 | 1.58 |
| Formic acid (99%) | 0.16 | 0.16 |
| Perfume oil (Table 15) | 25.00 | 24.74 |
| Polyisocyanate [2] | 1.90 | 1.41 |
| Cationic polymer [3] | 34.00 | 1.01 |
| Water | To balance | 71.10 |
| Total | 101.06 | 100.00 |

[1] Ambergum ™ 1221, 4%; Hercules Inc.
[2] Takenate ® D-110N (75%) trademark from: Mitsui Chemicals; trimethylol propane adduct of xylylene diisocyanate
[3] Salcare ® SC60: origin and trademark from Ciba (acrylamidopropyltrimonium chloride/acrylamide copolymer), 3% solution in water Example 9

Stability in AP-Roll on

Preparation of AP Roll on Base

A mixture of BRIJ 72 (3.25 g, Croda, UK), BRIJ721 (0.75 g, Croda, UK), and ARLAMOL E (4.00 g, Croda, UK), previously warmed up to 75° C., was added to water (51.00 g) under stirring. The mixture was homogenised for 10 minutes and then cooled down to room temperature under stiring. LOCRON L (40.00 g, Clariant, Switzerland) was added slowly at 45° C., the mixture was kept at room temperature. The capsule to dispersion of the present invention (circa 2.60 g) was added at 35° C. to afford a white liquid emulsion with a concentration of encapsulated perfume oil of 1%, a neutral odor (pH 4.2-4.7) and with a viscosity between 1000 and 2500 cPs (measured 24 to 48 h after production).

TABLE 34

| AP Roll on base composition | | |
| --- | --- | --- |
| Raw materials | Amount (g) | % (w/w) |
| BRIJ 72 | 3.25 | 3.17 |
| BRIJ 721 | 0.75 | 0.73 |
| ARLAMOL E | 4.00 | 3.90 |
| Water | 51.00 | 50.70 |
| LOCRON L | 40.00 | 39.00 |
| Capsule dispersion | 2.60 | 2.53 |
| TOTAL | 102.6 | 100 |

Perfume Leakage Measurement

Samples of AP Roll on base (1 g) were introduced in a GC vial capped with a septum. Vials were stabilized at 65° C. for 5 min under stirring. Sampling was done with SPME fiber assembly with a 85 μm polyacrylate coating for 10 min. Leakage of perfume from microcapsules was measured by gas chromatography (GC) using a GC system 6890N equipped with mass spectrometer detector 5973 (Agilent Technologies, USA) and a DB-1 MS column (30 m, i.d. 0.25 mm, film thickness 0.25 μm). The volatiles were analyzed by GC at 60° C. for 2 min and then heated to 250 at 7° C. min$^{-1}$, for a total run time of 29 min. Helium was the mobile gas phase (1.2 mL min-1, pressure 80.5 KPa, splitless). A calibration curve was measured with the free perfume oil.

TABLE 35

| Microcapsules | Acid | Leakage [wt %] |
| --- | --- | --- |
| Comparative B-7 | Acetic | 7.8 |
| Comparative E-7 | Acetic | 6.5 |
| B-6 | Acetic/Glyoxylic 50/50 | 1.2 |
| C-6 | Acetic/Glyoxylic 25/75 | 0.5 |
| E-6 | Acetic/Glyoxylic 10/90 | 0.0 |
| F-6 | Acetic/Glyoxylic 10/90 | 0.0 |
| G-6 | Acetic/Glyoxylic 10/90 | 0.0 |
| A-1 | Glyoxylic | 4.8 |
| B-1 | Glyoxylic | 0.2 |
| E-1 | Glyoxylic | 0.1 |
| F-1 | Glyoxylic | 0.8 |
| G-1 | Glyoxylic | 2.0 |
| H-1 | Glyoxylic | 0.4 |
| I-1 | Glyoxylic | 0.1 |
| J-1 | Glyoxylic | 0.0 |
| A-2 | Nitric | 0.0 |
| B-2 | Sulfuric | 0.1 |
| C-2 | Formic | 0.5 |
| D-2 | Hydrochloric | 0.0 |
| E-2 | Phosphoric | 0.0 |
| F-2 | Oxalic | 0.0 |
| G-2 | Citric | 0.0 |

It is apparent from these results that the presence of at least one protic acid having a pKa below 4.5 prevents the oil leakage from the microcapsules.

Example 10

Deposition on Hair

Preparation of Application Base

TABLE 36

| composition of shampoo base | |
|---|---|
| Ingredient | Composition [wt %] |
| A | |
| Water deionised | 44.9 |
| Quaternized hydroxyethyl cellulose[1] | 0.3 |
| Glycerin 85% (Origin: Schweizerhall) | 1.0 |
| Glydant (Origin: Lonza) | 0.2 |
| B | |
| Texapon NSO IS (Origin: Cognis) | 28.0 |
| Tego Betain F 50 (Origin: Goldschmidt AG) | 3.2 |
| Amphotensid GB 2009 (Origin: Zschimmer & Schwarz) | 2.0 |
| C | |
| Texapon NSO IS (Origin: Cognis) | 4.0 |
| Monomuls 90 L-12 (Origin: Gruenau) | 0.3 |
| D | |
| Water deionised | 1.0 |
| NIPAGIN Monosodium (Origin: NIPA) | 0.1 |
| E | |
| Sodium Chloride 10% aq. sln | 15.0 |
| TOTAL | 100.0 |

[1]Ucare™ Polymer JR-400 (origin: Noveon)

Protocol of Deposition Measurement

1) Miniature hair swatches (500 mg) was wetted with tap water (40 mL) at 37° C. by syringe, and then squeezed once.

2) Wet hair swatch was pretreated with unperfumed base (0.2 mL), five horizontal rubbing passes followed by five vertical rubbing passes; then it was rinsed with tap water at 37° C. (100 mL), and finally it was squeezed once.

3) Perfumed base (0.2 mL, capsules added to obtain 0.2 wt % perfume in the base) was applied to hair swatch with 10 horizontal rubbing passes followed by 10 vertical rubbing passes.

4) Hair swatches were rinsed with tap water at 37° C. (100 mL) added by separation funnel, 7 cm from orifice, shake gently 5 times.

5) Hair swatches were cut into 20 mL vials and dried overnight at 65° C. The hair mass was determined.

6) EtOH (5 mL) was added into vials, which were sonicated for 15 min, then shake on plate for 30 min, and filtered.

7) For controls dried overnight at 65° C.; EtOH (5 mL) was added to vials, which were sonicated for 15 min, shake on plate for 30 min, and filtered.

8) Uvinul A plus was quantified by HPLC.

TABLE 37

| Deposition of microcapsules on hair | |
|---|---|
| Microcapsules | Deposition of oil [wt %] |
| A-4 | 16.8 |
| B-4 | 24.0 |
| C-4 | 21.3 |
| D-4 | 23.7 |
| E-4 | 33.2 |
| F-4 | 22.3 |
| G-4 | 13.5 |
| H-4 | 23.3 |
| J-4 | 30.5 |
| K-4 | 12.0 |
| L-4 | 26.1 |
| M-4 | 28.7 |
| N-4 | 26.9 |
| O-4 | 18.5 |
| P-4 | 17.5 |
| Q-4 | 20.1 |
| R-4 | 14.3 |

These data underline that good deposition is obtained with the microcapsules according to the invention.

Example 11

Preparation of Shower Gel Base with Capsules

Capsules of the present invention were dispersed in shower gel base described in table 37 to obtain a concentration of encapsulated perfume oil at 0.25%. Shower gel base and capsules were stored at 50° C. for one week.
Table 38: Shower Gel Formulation

TABLE 38

| Shower gel formulation | |
|---|---|
| Ingredients | % w/w |
| 1. Water deionised | 49.35 |
| 2. EDETA B Powder Tetrasodium EDTA (Origin: BASF) | 0.05 |
| 3. Carbopol ® Aqua SF-1 Polymer Acrylates copolymer (Origin: Noveon) | 6.00 |
| 4. Zetesol AO 328 U Sodium C12-C15 Pareth Sulfate (Origin: Zschimmer & Schwarz) | 35.00 |
| 5. Sodium hydroxide 20% aqueous solution | 1.00 |
| 6. Tego ® Betain F 50 Cocamidopropyl Betaine (Origin: Goldschmidt AG) | 8.00 |
| 7. Kathon CG Methylchloroisothiazolinone and methylisothiazolinone (Origin: Rohm & Haas) | 0.10 |
| 8. Citric acid 40% aqueous solution | 0.50 |

Stability in Shower Gel Application

Shower gel base containing capsules (1 g) was introduced into a 20 mL vial hermetically closed with a rubber septum. Vial was stabilized at 65° C. for 5 minutes. A solid phase microextraction (SPME fiber assembly, 85 μm polyacrylate coating) needle was introduced into the vial through the septum and kept above the shower gel for 10 minutes. Needle was then injected in GC injector equipped with a DB-1 MS column (Origin: Agilent, length 30 m, inner diameter 25 mm, film thickness 0.25 μm). Helium flow was 1.2 mL/min with a pressure of 80.5 kPa and split ratio was 20. Temperature of the oven was 60° C. and it warmed up to 250° C. at 7° C./min.

TABLE 39

| Stability (1 week - 50° C.) | |
|---|---|
| Sample | Leakage (%) |
| Capsule A-8 | 9.1 |
| Capsule B-8 | 16.0 |
| Capsule C-8 | 14.0 |
| Capsule D-8 | 18.2 |
| Capsule E-8 | 9.3 |
| Capsule F-8 | 0.0 |
| Capsule G-8 | 8.0 |
| Capsule H-8 | 11.9 |
| Capsule I-8 | 14.5 |
| Capsule J-8 | 0.0 |
| Capsule K-8 | 0.1 |
| Capsule L-8 | 8.0 |
| Capsule M-8 | 7.0 |
| Capsule N-8 | 6.0 |
| Capsule O-8 | 9.0 |
| Capsule P-8 | 8.0 |
| Capsule Q-8 | 10.0 |

Capsules prepared with glyoxylic acid or stronger acids are stable in the shower gel base.

Example 12

Shampoo with Microcapsules Prepared According to the Process of the Invention Preparation of Microcapsules for Shampoo Application Microcapsules A9:

A solution of Ambergum™ 1221 (carboxymethyl cellulose, trademark from Hercules Inc.) in water was added in a beaker of 100 mL. The pH value was adjusted with glyoxylic acid to 3.89. This solution was kept at 25° C. before the preparation of the emulsion. A solution of a perfume oil (see table 40) and polyisocyanate (see Table 2) was added into the beaker and shear with UltraTurrax at 24000 rpm for 2 min. The emulsion was transferred into a 250 mL reactor and heated at 45° C. for 1 h, then at 60° C. for 1 h, and at 80° C. for 2 h. A solution of cationic copolymer (Table 41) was added and the reaction was stirred at 80° C. for 1 h. The reaction mixture was finally cooled down to RT (pH=3.90).

TABLE 40

| Composition of perfume oil | |
|---|---|
| Raw material | Qty (g) |
| Amyl Acetate | 1 |
| Pipol Acetate | 0.67 |
| Prenyl Acetate | 0.76 |
| Hexyl Acetate | 0.28 |
| Hexylcinnamic Aldehyde | 9.63 |
| Ethyl 2-methyl-pentanoate 1) | 1.3 |
| Benzyl Benzoate | 1.63 |
| Carbinol Butyrate | 7.63 |
| Ethyl Caproate | 0.13 |
| Methyl Cinnamate | 0.19 |
| Allyl Cyclohexylpropionate | 2.73 |
| Damascenone | 0.2 |
| Delta Damascone | 0.21 |
| Dodecalactone | 0.22 |
| Floropal™ 2) | 0.54 |
| Galaxolide™ 3) | 20.08 |
| 2 Ethyl Methylbutyrate | 1.08 |
| Nectalactone | 9.9 |
| Ethyl Octylate | 4.03 |
| Hexyl Salicylate | 4.61 |
| Verdox™ 4) | 17.93 |
| 2,4-Dimethyl-3-cyclohexene-1-carbaldehyde 5) | 2.6 |
| Isopropyl Myristate | 11.66 |

1) Origin: Firmenich SA, Geneva, Switzerland
2) 2,4,6-Trimethyl-4-phenyl-1,3-dioxane, Origin Symrise
3) 4,6,6,7,8,8-Hexamethyl-1,3,4,6,7,8-hexahydrocyclopenta[g]isochromene, Origin International Flavors & Fragrances, USA
4) 2-tert-butyl-1-cyclohexyl acetate, Origin International Flavors & Fragrances, USA
5) Origin: Firmenich SA, Geneva, Switzerland

TABLE 41

| Capsule formulation | | |
|---|---|---|
| Raw materials | Amount (g) | % (w/w) |
| Water | To balance | To balance |
| Carboxymethyl cellulose (Ambergum™ 1221, 4%) | 40.00 | 1.58 |
| 2-Oxoacetic acid (50%) | 0.51 | 0.25 |
| Perfume oil | 25.00 | 24.65 |
| Polyisocyanate [1] | 1.90 | 1.41 |
| Cationic copolymer [2] | 34.00 | 1.01 |
| Total | 101.41 | 100.00 |

[1] Takenate® D-110N (75%) - trimethylol propane adduct of xylylene diisocyanate, trademark from: Mitsui Chemicals
[2] Salcare® SC60: origin and trademark from Ciba (acrylamidopropyltrimonium chloride/acrylamide copolymer), 3% solution in water Microcapsules B9:

Microcapsules B9 were prepared according to the protocol described for Microcapsules A9. Solution of glyoxylic acid was replaced by a solution of oxalic acid (15.40 g, 0.1M in water, pH 4.04).

Microcapsules C9:

Microcapsules C9 were prepared according to the protocol described for Microcapsules A9. Solution of glyoxylic acid was replaced by citric acid (0.35 g, 99.5%, pH 4.08).

Microcapsules D9:

Microcapsules D9 were prepared according to the protocol described for Microcapsules A9. Solution of glyoxylic acid was replaced by DL malic acid (0.34 g, pH 4.08).

Microcapsules E9:

Microcapsules E9 were prepared according to the protocol described for Microcapsules A9. Solution of glyoxylic acid was replaced by a solution of lactic acid (0.38 g, 90% in water, pH 4.08).

Microcapsules F9:

Microcapsules F9 were prepared according to the protocol described for Microcapsules A9. Solution of glyoxylic acid was replaced by a solution of phosphoric acid (0.29 g, 84% in water, pH 4.03).

Microcapsules G9:

Microcapsules G9 were prepared according to the protocol described for Microcapsules A9. Solution of glyoxylic acid was replaced by formic acid (0.16 g, pH 4.08).

Performance on Hair
Preparation of Application Base

TABLE 42 composition of shampoo base

| Ingredient | Composition [wt %] |
|---|---|
| A | |
| Water deionised | 44.9 |
| Quaternized hydroxyethyl cellulose[1)] | 0.3 |
| Glycerin 85% (Origin: Schweizerhall) | 1.0 |
| Glydant (Origin: Lonza) | 0.2 |
| B | |
| Texapon NSO IS (Origin: Cognis) | 28.0 |
| Tego Betain F 50 (Origin: Goldschmidt AG) | 3.2 |
| Amphotensid GB 2009 (Origin: Zschimmer & Schwarz) | 2.0 |
| C | |
| Texapon NSO IS (Origin: Cognis) | 4.0 |
| Monomuls 90 L-12 (Origin: Gruenau) | 0.3 |
| D | |
| Water deionised | 1.0 |
| NIPAGIN Monosodium (Origin: NIPA) | 0.1 |
| E | |
| Sodium Chloride 10% aq. sln | 15.0 |
| TOTAL | 100.0 |

[1)]Ucare ™ Polymer JR-400 (origin: Noveon)

Protocol of Performance Measurement

Capsules were incorporated at a dosage corresponding to 0.2% of perfume in the shampoo base and macerated at room temperature for at least 24 hours and for one month at 45° C. Two dry hair swatches (10 g, Kerling Int., Cat. No.: 826500, Euro-Natural hair) were wet for 30 s under warm water (about 37° C.) and then were washed with 1 g of shampoo per 10 g of hair for 30 s. with gentle rubbing between the fingers. The washed hair swatches were rinsed in one 1 L beaker previously filled with warm water. They were dipped into the beaker three times (three times in, three times out). Then they were dipped into the beaker and slowly moved back and forth three times in each direction, and finally rinsed for 30 s. (15 s. on each side) under running water (flow rate 4 L/min) without touching the swatches at all.

Excess of water was removed by squeezing of the swatch from the plastic part at the top to the end of the hair. Hair swatches were not touched anymore or squeezed out to remove excess water. A second wash with 1 g of shampoo for 30 s. was done and the above rinsing protocol was repeated. Hair swatches were put on the drying rack to air dry at room temperature for 24 hours.

Fragrance intensity of the hair swatches was evaluated before combing the hair according to the following perfume intensity scale: 1—Imperceptible, 2—Slightly perceptible, 3—Weak, 4—Medium, 5—Sustained, 6—Intense, 7—Very intense. Hair swatches were combed three times with the thin part of the comb. Perfume intensity just after combing the hair was evaluated according to the same scale. Once a hair swatch was touched, rubbed or combed, it could not be evaluated again for the "before combing" step. Thus at least two sets of hair swatches were prepared. One was never combed and used only for the "before combing" step. The other set was combed by a maximum of ten panelists for the "after combing" step. If more than ten panelists were required, another set of hair swatches was prepared for the "after combing" step. Throughout the washing protocol, hands were protected by gloves.

Results are given in the following table.

TABLE 43

Performance of microcapsules on hair

| Micro-capsules | Fresh capsules before rubbing | Fresh capsules after rubbing | Aged capsules 1 m at 45° C., before rubbing | Aged capsules 1 m at 45° C., after rubbing |
|---|---|---|---|---|
| A9 | 2.9 | 5.0 | 3.0 | 4.9 |
| B9 | 2.4 | 3.9 | 1.7 | 3.1 |
| C9 | 2.8 | 4.9 | 1.7 | 4.3 |
| D9 | 2.6 | 4.3 | 2.0 | 4.3 |
| E9 | 3.0 | 5.8 | 1.9 | 4.1 |
| F9 | 3.0 | 5.1 | 2.3 | 4.3 |
| G9 | 2.8 | 3.6 | 1.3 | 2.4 |

These examples underline that microcapsules of the invention show good olfactive performance even with aged sample.

Example 13

Fabric Softener Comprising Microcapsules Prepared by the Process of the Invention Preparation of Microcapsules
Microcapsules A10

A solution of Ambergum™ 1221 (carboxymethyl cellulose, trademark from Hercules Inc.) in water was added in a beaker of 100 mL. The pH value was adjusted with glyoxylic acid to 3.73. This solution was kept at 25° C. before the preparation of the emulsion. A solution of perfume oil (Table 44) and polyisocyanate (see Table 45) was added into the beaker and shear with UltraTurrax at 24000 rpm for 2 min. The emulsion was transferred into a 250 mL reactor and heated at 45° C. for 1 h, then at 60° C. for 1 h, and finally at 80° C. for 3 h. The reaction mixture was cooled down to RT (pH=3.87).

TABLE 44 perfume oil composition

| Raw materials | % |
|---|---|
| ETHYL 2 METHYLBUTYRATE | 1.40% |
| AMYL ACETATE | 0.90% |
| ALDEHYDE C 8 | 5.40% |
| EUCALYPTOL | 6.20% |
| AMYL BUTYRATE | 1.10% |
| 2,4-DIMETHYL-3-CYCLOHEXENE-1-CARBALDEHYDE [1)] | 3.00% |
| ALDEHYDE C 9 | 0.80% |
| ALDEHYDE C 10 | 10.60% |
| ISOBORNYL ACETATE | 7.10% |
| HELIOTROPIN [2)] | 0.35% |
| METHYLCINNAMIC ALDEHYDE | 0.65% |
| ALDEHYDE MNA | 6.30% |
| DELTA DAMASCONE | 0.50% |
| VERDYL ACETATE | 31.50% |
| (+−)-(3E)-4-(2,6,6-TRIMETHYL-2-CYCLOHEXEN-1-YL)-3-BUTEN-2-ONE (A) + (3E)-4-(2,6,6-TRIMETHYL-1-CYCLOHEXEN-1-YL)-3- | 0.35% |

TABLE 44-continued

| perfume oil composition | |
|---|---|
| Raw materials | % |
| BUTEN-2-ONE (B) 2-METHOXYNAPHTHALENE | 1.50% |
| ETHYL CINNAMATE | 0.80% |
| NEOBUTENONE ® [3] | 0.10% |
| METHYLIONONE ALPHA ISO | 2.70% |
| UNDECALACTONE GAMMA | 17.60% |
| BENZYL BENZOATE | 1.15% |
| Total | 100.00% |

[1] Origin: Firmenich SA, Geneva, Switzerland
[2] 1,3-Benzodioxole-5-carbaldehyde, Origin: Firmenich SA, Geneva, Switzerland
[3] 1-(5,5-dimethyl-1-cyclohexen-1-yl)-4-penten-1-one, Origin: Firmenich SA, Geneva, Switzerland

TABLE 45

| Capsule formulation | | |
|---|---|---|
| Raw materials | Amount (g) | % (w/w) |
| Water | To balance | To balance |
| Carboxymethyl cellulose (Ambergum™ 1221, 4%) | 40.00 | 2.37 |
| 2-Oxoacetic acid (50%) | 0.57 | 0.42 |
| Perfume oil (Table 44) | 25.00 | 37.10 |
| Polyisocyanate [1] | 1.90 | 2.11 |
| Total | 67.47 | 100.00 |

[1] Takenate ® D-110N (75%) - trimethylol propane adduct of xylylene diisocyanate, trademark from: Mitsui Chemicals Comparative Microcapsules B10

A solution of carboxymethyl cellulose (Ambergum™ 1221; Hercules Inc.) in water was added in a beaker of 100 mL. The pH value was adjusted with acetic acid to 4.01. This solution was kept at room temperature before the preparation of the emulsion. A solution of perfume oil and polyisocyanate was added into the beaker and shear with Ultra-Turrax at 24000 rpm for 2 min. The emulsion was transferred into a 250 mL reactor and heat at 45° C. for 1 h, then at 60° C. for 1 h, and finally at 80° C. for 3 h. The reaction mixture was cooled down to RT (pH=4.03).

TABLE 46

| Capsule formation | | |
|---|---|---|
| Raw materials | Amount (g) | % (w/w) |
| Carboxymethyl cellulose [1] | 40.00 | 2.37 |
| Acetic acid | 0.70 | 1.04 |
| Perfume oil (Table 44) | 25.00 | 36.98 |
| Polyisocyanate [2] | 1.90 | 2.11 |
| Water | To balance | 57.50 |
| Total | 67.6 | 100.00 |

[1] Ambergum ™ 1221, 4%; Hercules Inc.
[2] Takenate ® D-110N (75%) trademark from: Mitsui Chemicals; trimethylol propane adduct of xylylene diisocyanate Softener Composition A concentrated unperfumed fabric softener base was prepared by admixing the ingredients listed in Table 47, in the amounts indicated. The percentages are defined by weight relative to the total weight of the unperfumed fabric softener base.

TABLE 47

| Formulation of the concentrated unperfumed fabric softener base (pH ~2.85) | |
|---|---|
| Ingredient | % |
| Stepantex VL90 A Diester Quat[1] | 16.50 |
| Proxel GXL[2] | 0.04 |
| CaCl$_2$ (10% aqueous solution) | 0.20 |
| Water | 83.26 |

[1] Origin: Stepan
[2] Origin: Avecia

Softeners were prepared by adding capsules A10 and comparative capsules B10 at 0.45% by weight, relative to the total weight of the softener into the unperfumed softener base of Table 47 under gentle shaking.

Storage Stability Performance

The storage stability of the capsules A10 (glyoxylic acid) in the above fabric-softener was evaluated after two weeks storage at 43° C. Storage stability of comparative capsules B10 (acetic acid) was also evaluated. The amount of perfume (see table 44) having leaked out of the capsules overtime was measured by solvent extraction and GC-MS analysis. The results are summarized in the following table 48.

TABLE 48

| Storage stability of capsules | |
|---|---|
|  | % perfume leaking out of the capsule upon storage in softener for 2 weeks at 43° C. |
| Comparative capsules B10 (acetic acid) | >90% |
| Capsules A10 (glyoxylic acid) | 22% |

The above results show that the stability of microcapsules prepared by the process of the invention is significantly higher than the comparative microcapsules.

Olfactive Performance

Wash & Rinse Protocol:

Cotton terry towels (20 pieces, 18 cm*18 cm, about 30 g each) were washed with 30 g of unperfumed detergent in a European washing machine (Miele Novotronic W300-33CH) at 40° C. using the short cycle program. The wash was followed by a rinse at 900 rpm with 12.7 g of above concentrated fabric-softener which had been stored for 2 weeks at 43° C. The terry towels were then line dried for 24 hours before being evaluated by a panel of 20 trained panelists. The panelists were asked to rate the odor intensity of the towels after gentle rubbing of the fabrics by hand on a scale from 1 to 10, 1 corresponding to odorless and 10 corresponding to a very strong odor.

Results

Panelists find that:

1/With fresh products, after drying, fabrics which have been washed and conditioned with capsules A10 of the invention deliver a strong perfume boost upon rubbing. Fabrics which have been washed and conditioned with comparative capsules B10 deliver a stronger perfume impact before rubbing but a much lower boost upon rubbing, indicating a poorer stability of the capsules in the washing machine.

2/With softeners aged for 2 weeks at 43° C., after drying, fabrics which have been washed and conditioned with capsules A10 of the invention still deliver a strong perfume boost upon rubbing, only slightly reduced versus fresh and in line with good analytical perfume stability. On the other hand, fabrics which have been washed and conditioned with comparative capsules B10 deliver a stronger perfume impact before rubbing but no boost at all upon rubbing, again fully consistent with the very poor stability of these capsules in the fabric-softener base at 43° C.

Example 14

AP Roll-on Comprising Microcapsules Prepared by the Process of the Invention

Preparation of Microcapsules for AP Roll on Application
Microcapsules A11

A solution of Ambergum™ 1221 (carboxymethyl cellulose, trademark from Hercules Inc.) in water was added in a beaker of 100 mL. The pH value was adjusted with a solution of glyoxylic acid to 3.82. This solution was kept at 25° C. before the preparation of the emulsion. A solution of perfume oil (see table 49) and polyisocyanate (see Table 50) was added into the beaker and shear with UltraTurrax at 24000 rpm for 2 min. The emulsion was transferred into a 250 mL reactor and heated at 45° C. for 1 h, then at 60° C. for 1 h, and at 80° C. for 2 h. A solution of cationic copolymer was added and the reaction was stirred at 80° C. for 1 h. The reaction mixture was finally cooled down to RT (pH=3.96).

TABLE 49

Perfume oil composition

| Ingredients | % in oil |
| --- | --- |
| Ethyl 2-methyl-pentanoate | 0.25 |
| (Z)-3-hexen-1-ol acetate | 0.30 |
| 2,4-Dimethyl-3-cyclohexene-1-carbaldehyde | 1.25 |
| Rose oxide | 0.40 |
| Hexyle Isobutyrate | 3.80 |
| Menthone | 0.50 |
| Menthol | 3.20 |
| linallyle acetate | 10.20 |
| carbinol BDM acetate | 2.05 |
| terpenyle acetate | 9.50 |
| citronellyle acetate | 7.30 |
| verdyle acetate | 3.00 |
| nopyle acetate | 7.60 |
| béta ionone | 0.50 |
| verdyle Propionate | 4.20 |
| Hedione ®[1] | 11.00 |
| Ald hexylcinnamique | 13.50 |
| Tinogard ®DA | 0.50 |
| Tinogard ® TT DD | 0.20 |
| 4-methyl-2,6-bis(2-methyl-2-propanyl)phenol | 0.10 |
| Neobutenone ®[2] | 0.10 |
| (1'R)-2-[2-(4'-methyl-3'-cyclohexen-1'-yl)propyl]cyclopentanone | 9.40 |
| MIP Isopropyl Myristate | 11.15 |

[1] Methyl dihydrojasmonate, Origin: Firmenich SA, Geneva, Switzerland
[2] 1-(5,5-dimethyl-1-cyclohexen-1-yl)-4-penten-1-one, Firmenich SA, Geneva, Switzerland

TABLE 50

Capsule formulation

| Raw materials | Amount (g) | % (w/w) |
| --- | --- | --- |
| Water | To balance | To balance |
| Carboxymethyl cellulose (Ambergum™ 1221, 4%) | 40.00 | 2.37 |
| 2-Oxoacetic acid (50%) | 0.51 | 0.38 |
| Perfume oil (see table 49) | 25.00 | 37.09 |
| Polyisocyanate[1] | 1.90 | 2.11 |
| Total | 67.41 | 100.00 |

[1] Takenate ® D-110N (75%) - trimethylol propane adduct of xylylene diisocyanate, trademark from: Mitsui Chemicals Microcapsules B11
Microcapsules B11 were prepared according to the protocol described for Microcapsules A11. Solution of glyoxylic acid and carboxymethyl cellulose was warmed up to 60° C. for 2 h.

Microcapsules C11:
Microcapsules C11 were prepared according to the protocol described for Microcapsules A11. Solution of glyoxylic acid was replaced by a mixture of acetic acid (0.12 g) and solution of glyoxylic acid (50 wt %, 0.36 g)

Microcapsules D11:
Microcapsules D11 were prepared according to the protocol described for Microcapsules A11. Solution of glyoxylic acid was replaced by citric acid (0.35 g).

Microcapsules E11:
Microcapsules E11 were prepared according to the protocol described for Microcapsules A11. Solution of glyoxylic acid was replaced by a solution of phosphoric acid (84%, 0.29 g).

Comparative Microcapsules G11:
A solution of carboxymethyl cellulose (Ambergum™ 1221; Hercules Inc.) in water was added in a beaker of 100 mL. The pH value was adjusted with acetic acid to 4.01. This solution was kept at room temperature before the preparation of the emulsion. A solution of perfume oil (see table 49) and polyisocyanate was added into the beaker and shear with UltraTurrax at 24000 rpm for 2 min. The emulsion was transferred into a 250 mL reactor and heat at 45° C. for 1 h, then at 60° C. for 1 h, and finally at 80° C. for 3 h. The reaction mixture was cooled down to RT (pH=4.03).

TABLE 51

Capsule formation

| Raw materials | Amount (g) | % (w/w) |
| --- | --- | --- |
| Carboxymethyl cellulose[1] | 40.00 | 2.37 |
| Acetic acid | 0.70 | 1.04 |
| Perfume oil (Table 49) | 25.00 | 36.98 |
| Polyisocyanate[2] | 1.90 | 2.11 |
| Water | To balance | 57.50 |
| Total | 67.6 | 100.00 |

[1] Ambergum™ 1221, 4%; Hercules Inc.
[2] Takenate ® D-110N (75%) trademark from: Mitsui Chemicals; trimethylol propane adduct of xylylene diisocyanate Stability in AP Roll on
Preparation of AP Roll on Base A mixture of BRIJ 72 (3.25 g, Croda, UK), BRIJ721 (0.75 g, Croda, UK), and ARLAMOL E (4.00 g, Croda, UK), previously warmed up to 75° C., was added to water (51.00 g) under stirring. The mixture was homogenised for 10 minutes and then cooled down to room temperature under stiring. LOCRON L (40.00 g, Clariant, Switzerland) was added slowly at 45° C., the mixture was kept at room temperature. The perfume oil (1.00 g, Firmenich SA, Switzerland) or the capsule dispersion of the present invention (2.60 g) was finally added at 35° C. to afford a white liquid emulsion with a neutral odor (pH 4.2-4.7) and with a viscosity between 1000 and 2500 cPs (measured 24 to 48 h after production).

Preparation of AP Roll on Application

Capsule dispersions (0.55 g) were introduced in an AP Roll on base UBK 99 032 (50 g, Table), described above. The base and the dispersion were stirred at 500 rpm and room temperature for 5 min with a dissolver stirrer (R-1303, IKA, Germany) and an overhead stirrer (Eurostar, IKA, Germany). Samples were stored at 25° C. for two weeks.

Perfume Leakage Measurement

Samples of AP Roll on base (1 g) were introduced in a GC vial capped with a septum. Vials were stabilized at 65° C. for 5 min under stirring. Sampling was done with SPME fiber assembly with a 85 microns polyacrylate coating for 10 min. Leakage of perfume from microcapsules was measured by gas chromatography (GC) using a GC system 6890N equipped with mass spectrometer detector 5973 (Agilent Technologies, USA) and a DB-1 MS column (30 m, i.d. 0.25 mm, film thickness 0.25 μm). The volatiles were analyzed by GC at 60° C. for 2 min and then heated to 250 at 7° C. min-1, for a total run time of 29 min. Helium was the mobile gas phase (1.2 mL min-1, pressure 80.5 KPa, splitless). A calibration curve was measured with the free perfume oil.

TABLE 51

Stability measurements in AP Roll on base at 45° C. (one month at 45° C.)

| Microcapsules | % |
|---|---|
| Microcapsules A11 | 2.6 |
| Microcapsules B11 | 1.1 |
| Microcapsules C11 | 3.7 |
| Microcapsules D11 | 1.8 |
| Microcapsules E11 | 0.8 |
| Comparative capsules G11 | 44.9 |

The above results show that the stability of microcapsules prepared by the process of the invention is significantly higher than the comparative microcapsules.

What is claimed is:

1. A process for the preparation of a melamine-formaldehyde free poly(urea-urethane) core-shell microcapsule slurry comprising the steps of:
   1) admixing an oil comprising an active ingredient with at least one polyisocyanate having at least three isocyanate functional groups to form an oil phase, provided that the oil phase is free from diisocyanate;
   2) preparing a water phase under acidic conditions, comprising at least one anionic biosourced polyol and a catalyst comprising a protic acid having a pKa below 4.5;
   3) adding the oil phase to the water phase to form an oil-in-water dispersion;
   4) performing a curing step to form a microcapsule slurry;
   5) optionally adding at least one cationic copolymer to the capsule slurry;

the process being performed without substantial amount of amine or polyamine being added at any stage of the process.

2. The process according to claim 1, wherein the anionic biosourced polyol is selected from the group consisting of lignin, lignin sulfate, carboxymethyl cellulose, alginic acid sodium salt, polygalacuronic acid, dextran sulphate sodium salt and mixtures thereof.

3. The process according to claim 1, wherein the protic acid is selected from the group consisting of glyoxylic acid, citric acid, tartaric acid, fumaric acid, salicylic acid, sulfuric acid, phosphoric acid, nitric acid, formic acid, chlorohydric acid, malic acid, lactic acid, oxalic acid and mixtures thereof.

4. The process according to claim 1, wherein step 2 further comprises curing the water phase at 45-60° C. for 30 min. to 2 hours.

5. The process according to claim 1, wherein step 4 consists in performing interfacial polymerisation at 60-80° C. for 1 to 4 hours.

6. The process according to claim 1, further comprising the step of drying the capsule slurry to obtain dried microcapsules.

7. The process according to claim 1, wherein the at least one polyisocyanate having at least three isocyanate functional groups is present in an amount comprised between 1 and 15 wt % of the oil phase.

8. The process according to claim 1, wherein the at least one polyisocyanate having at least three isocyanate functional groups comprises an aromatic polyisocyanate.

9. The process according to claim 1, wherein the oil phase consists essentially of a perfume or flavour oil with the at least one polyisocyanate having at least three isocyanate functional groups.

10. The process of claim 1, wherein the active ingredient is a perfume.

11. The process of claim 1, wherein the acidic conditions are below pH 4.5.

* * * * *